(12) United States Patent
Watanabe

(10) Patent No.: US 12,254,626 B2
(45) Date of Patent: Mar. 18, 2025

(54) IMAGE PROCESSING DEVICE, ENDOSCOPE SYSTEM, AND IMAGE PROCESSING METHOD

(71) Applicant: FUJIFILM Corporation, Tokyo (JP)

(72) Inventor: Hiroki Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 348 days.

(21) Appl. No.: 17/817,846

(22) Filed: Aug. 5, 2022

(65) Prior Publication Data

US 2022/0383492 A1 Dec. 1, 2022

Related U.S. Application Data

(63) Continuation of application No. PCT/JP2021/002286, filed on Jan. 22, 2021.

(30) Foreign Application Priority Data

Feb. 7, 2020 (JP) .................................. 2020-019803

(51) Int. Cl.
*A61B 5/00* (2006.01)
*A61B 1/00* (2006.01)
*G06T 7/00* (2017.01)

(52) U.S. Cl.
CPC ...... *G06T 7/0012* (2013.01); *A61B 1/000096* (2022.02); *G06T 2207/10068* (2013.01); *G06T 2207/20081* (2013.01); *G06T 2207/30028* (2013.01); *G06T 2207/30101* (2013.01); *G06T 2207/30168* (2013.01)

(58) Field of Classification Search
None
See application file for complete search history.

(56) References Cited

U.S. PATENT DOCUMENTS

| | | | |
|---|---|---|---|
| 8,185,185 B2* | 5/2012 | Gilreath | G16H 15/00 600/407 |
| 9,324,145 B1 | 4/2016 | Cherevatsky et al. | |
| 9,456,755 B2* | 10/2016 | Soykan | A61B 5/318 |

(Continued)

FOREIGN PATENT DOCUMENTS

| | | |
|---|---|---|
| JP | 2006-122502 A | 5/2006 |
| JP | 2006-288612 A | 10/2006 |

(Continued)

OTHER PUBLICATIONS

Imai, Yoshiro; Image Processing Device, Endoscope System, and Image Processing Method; 2018 (Year: 2018).*

(Continued)

*Primary Examiner* — Marcellus J Augustin
(74) *Attorney, Agent, or Firm* — Studebaker Brackett PLLC

(57) ABSTRACT

There is provided an image processing device comprising a processor, in which the processor acquires a plurality of endoscopic images obtained by picking up images of an observation target with an endoscope, calculates a raw score related to a determination of a severity or a stage of a disease of the observation target, on the basis of each of the endoscopic images, decides a final score on the basis of the raw score, and performs control to display the final score and/or a change over time of the final score in real time on a display.

18 Claims, 18 Drawing Sheets

(56) References Cited

U.S. PATENT DOCUMENTS

| | | | |
|---|---|---|---|
| 9,784,665 B1 * | 10/2017 | Milici | G06V 20/698 |
| 2006/0154210 A1 * | 7/2006 | Martin | A61B 5/00 |
| | | | 433/215 |
| 2007/0191677 A1 | 8/2007 | Nishimura et al. | |
| 2008/0086028 A1 | 4/2008 | Matsui | |
| 2009/0051695 A1 | 2/2009 | Matsuda | |
| 2010/0030803 A1 * | 2/2010 | Rothenberg | G06Q 10/06 |
| | | | 707/E17.044 |
| 2016/0174886 A1 | 6/2016 | Shiraishi | |
| 2017/0258296 A1 | 9/2017 | Kaku | |
| 2018/0211385 A1 | 7/2018 | Imai | |
| 2018/0214005 A1 | 8/2018 | Ebata | |
| 2019/0059707 A1 | 2/2019 | Watanabe | |
| 2020/0279368 A1 * | 9/2020 | Tada | A61B 1/00016 |
| 2022/0020496 A1 * | 1/2022 | Saito | G06T 7/0012 |

FOREIGN PATENT DOCUMENTS

| | | |
|---|---|---|
| JP | 2009-050321 A | 3/2009 |
| JP | 2015-085152 A | 5/2015 |
| JP | 2016-144626 A | 8/2016 |
| JP | 2016-214637 A | 12/2016 |
| JP | 2019-037688 A | 3/2019 |
| JP | 2019-111040 A | 7/2019 |
| WO | 2017/057414 A1 | 4/2017 |
| WO | 2017/057574 A1 | 4/2017 |

OTHER PUBLICATIONS

An Office Action; "Notice of Reasons for Refusal," mailed by the Japanese Patent Office on Aug. 1, 2023, which corresponds to Japanese Patent Application No. 2021-575725 and is related to U.S. Appl. No. 17/817,846; with English language translation.

Hideki Ishikawa et al.; "Problems related to judgment of cure of ulcerative colitis"; Gastroenterological Endoscopy, Jan. 20, 1990, vol. 32, No. 1, pp. 262-263.

International Search Report issued in PCT/JP2021/002286; mailed Apr. 13, 2021.

International Preliminary Report On Patentability (Chapter I) and Written Opinion of the International Searching Authority issued in PCT/JP2021/002286; issued Jul. 28, 2022.

The extended European search report issued by the European Patent Office on Jun. 29, 2023, which corresponds to European Patent Application No. 17817846-1126 and is related to U.S. Appl. No. 17/817,846.

An Office Action; "Notice of Reasons for Refusal," mailed by the Japanese Patent Office on Jan. 9, 2024, which corresponds to Japanese Patent Application No. 2021-575725 and is related to U.S. Appl. No. 17/817,846; with English language translation.

* cited by examiner

A # IMAGE PROCESSING DEVICE, ENDOSCOPE SYSTEM, AND IMAGE PROCESSING METHOD

CROSS-REFERENCE TO RELATED APPLICATIONS

This application is a Continuation of PCT International Application No. PCT/JP2021/002286 filed on 22 Jan. 2021, which claims priority under 35 U.S.C § 119(a) to Japanese Patent Application No. 2020-019803 filed on 7 Feb. 2020. The above application is hereby expressly incorporated by reference, in its entirety, into the present application.

BACKGROUND OF THE INVENTION

1. Field of the Invention

The present invention relates to an image processing device, an endoscope system, and an image processing method that perform diagnosis support by using an endoscopic image captured by an endoscope.

2. Description of the Related Art

In a medical field, a diagnosis using an endoscope system comprising a light source device, an endoscope, and a processor device has been widely performed. In the diagnosis using the endoscope system, a computer-aided diagnosis (CAD) technology for performing appropriate image processing on an image (hereinafter, referred to as an endoscopic image) obtained by imaging an observation target with the endoscope to determine the stage or the like of a specific disease of the observation target has been developed. With the CAD used, for example, the severity of the disease, a score associated with a pathological result, or the like is calculated in real time or near real time and is displayed on a display or the like.

Techniques for more convenient use of the CAD are disclosed. For example, there is known an image analysis device capable of automatically discriminating between a super-magnified image and a non-magnified image for CAD using a super-magnified image in an endoscopic image (JP2019-111040A).

SUMMARY OF THE INVENTION

In a real-time CAD using an endoscopic image, a stable determination result may not be obtained because the position of an observation target in the endoscopic image is easily changed. For example, in a case of determining the stage of ulcerative colitis by performing image processing on the endoscopic image, the determination result of the stage may be not stable because the determination result is also finely changed in a case where an observation position is finely changed. Therefore, it is desired to obtain a stable determination result in order to make the CAD easier to use.

The present invention has been made in view of the above circumstances, and an object of the present invention is to provide an image processing device, an endoscope system, and an image processing method that stably display a determination result regarding a disease by using an endoscopic image.

The present invention relates to an image processing device comprising a processor. The processor acquires a plurality of endoscopic images obtained by picking up images of an observation target at times different from each other with an endoscope, calculates a raw score related to a determination of a severity or a stage of a disease of the observation target, on the basis of each of the endoscopic images, decides a final score on the basis of the raw score, and performs control to display the final score and/or a change over time of the final score in real time on a display.

It is preferable that the processor calculates two or more types of raw scores different from each other.

It is preferable that the processor calculates the raw score on the basis of a first feature amount obtained by analyzing the endoscopic image.

It is preferable that the first feature amount is an amount related to a superficial blood vessel dense part, an intramucosal hemorrhage part, or an extramucosal hemorrhage part included in the endoscopic image.

It is preferable that the processor executes a trained first machine learning model generated by an input of a past endoscopic image associated with the raw score to a machine learning model, and calculates the raw score on the basis of the endoscopic image.

It is preferable that the processor decides the final score from the raw score that is calculated on the basis of a plurality of the endoscopic images acquired in a predetermined period before a point in time at which the final score is decided.

It is preferable that the processor decides the final score by performing a moving average, or FIR filtering or IIR filtering of a plurality of the raw scores.

It is preferable that the processor decides the final score on the basis of the raw score calculated immediately before or immediately after a point in time at which the final score is decided.

It is preferable that the processor discriminates, for each endoscopic image, whether the endoscopic image is suitable or unsuitable for the calculation of the raw score, and defines the raw score to be uncalculated for the endoscopic image discriminated to be unsuitable for the calculation of the raw score.

It is preferable that the processor discriminates whether the endoscopic image is suitable or unsuitable for the calculation of the raw score, on the basis of a second feature amount of the endoscopic image.

It is preferable that the second feature amount is an amount related to at least one selected from the group consisting of halation distribution, spatial frequency distribution, brightness value distribution, shadow distribution, a magnification ratio indicator, and reflected light distribution of illumination light of the endoscopic image, the illumination light being emitted to the observation target.

It is preferable that the processor executes a trained second machine learning model generated by an input of a past endoscopic image to a machine learning model, the past endoscopic image being associated with whether the endoscopic image is suitable or unsuitable for the calculation of the raw score, and discriminates whether the endoscopic image is suitable or unsuitable for the calculation of the raw score.

It is preferable that the processor decides the final score on the basis of the raw score except for the raw score to be uncalculated.

It is preferable that the processor defines the final score to be uncalculated in a case where the number of the raw scores except for the raw score to be uncalculated is a predetermined number or less, a case where the number of the raw scores to be uncalculated is a predetermined number or more, the raw scores being based on the plurality of endoscopic images acquired in the predetermined period, or a case where a ratio of the number of the raw scores to be uncalculated to the number of the raw scores based on the plurality of endoscopic images acquired in the predetermined period is a predetermined value or more.

It is preferable that the change over time of the final score is displayed by at least one graph showing a relationship between the final score and a decision time of the final score.

It is preferable that the processor determines a site of the observation target included in the endoscopic image by performing image analysis on the endoscopic image, and the change over time of the final score is displayed by at least one graph showing a relationship between the final score, and a decision time of the final score and the site.

It is preferable that the processor gives an instruction to acquire a still image, and performs control to display the final score and/or the change over time of the final score in a case where the instruction is given.

It is preferable that the disease is ulcerative colitis.

Further, the present invention relates to an endoscope system comprising: an endoscope that picks up an image of an observation target; and an image processing device provided with a processor. The processor acquires a plurality of endoscopic images obtained by picking up images of an observation target at times different from each other, calculates a raw score related to a determination of a severity or a stage of a disease of the observation target, on the basis of each of the endoscopic images, decides a final score on the basis of the raw score, and performs control to display the final score and/or a change over time of the final score in real time on a display.

Further, the present invention relates to an image processing method comprising: an image acquisition step of acquiring a plurality of endoscopic images obtained by picking up images of an observation target at times different from each other; a raw score calculation step of calculating a raw score related to a determination of a severity or a stage of a disease of the observation target, on the basis of each of the endoscopic images; a final score decision step of deciding a final score on the basis of the raw score; and a display control step of performing control to display the final score and/or a change over time of the final score in real time on a display.

According to the present invention, it is possible to stably display a determination result regarding a disease by using an endoscopic image.

DESCRIPTION OF THE PREFERRED EMBODIMENTS

Figure 1:
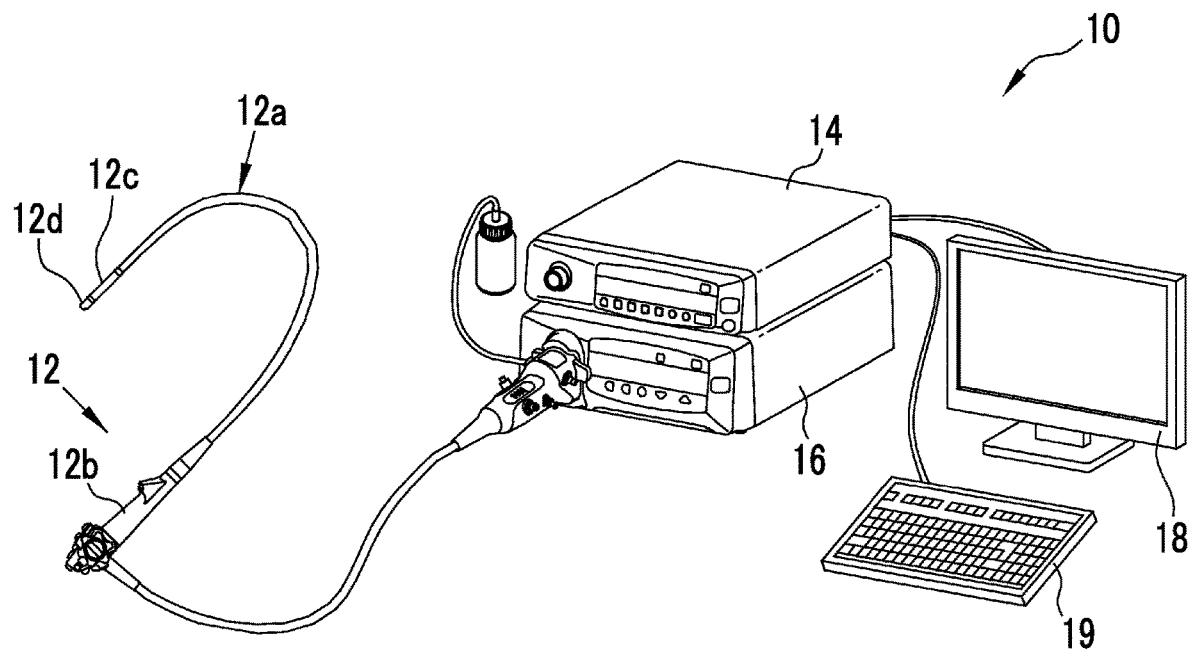
FIG. 1 is an external view of an endoscope system.

In FIG. 1, an endoscope system 10 includes an endoscope 12, a light source device 14, a processor device 16, a display 18, and a console 19. The endoscope 12 is optically connected to the light source device 14 and is electrically connected to the processor device 16. The endoscope 12 includes an insertion part 12a that is inserted into a body of an observation target, an operation part 12b that is provided at the proximal end portion of the insertion part 12a, and a bendable portion 12c and a distal end portion 12d that are provided in the insertion part 12a on the distal end side. An angle knob 12e (see FIG. 2) of the operation part 12b is operated so that the bendable portion 12c is operated to be bent. The bendable portion 12c is operated to be bent so that the distal end portion 12d is made to face in a desired direction.

Figure 2:
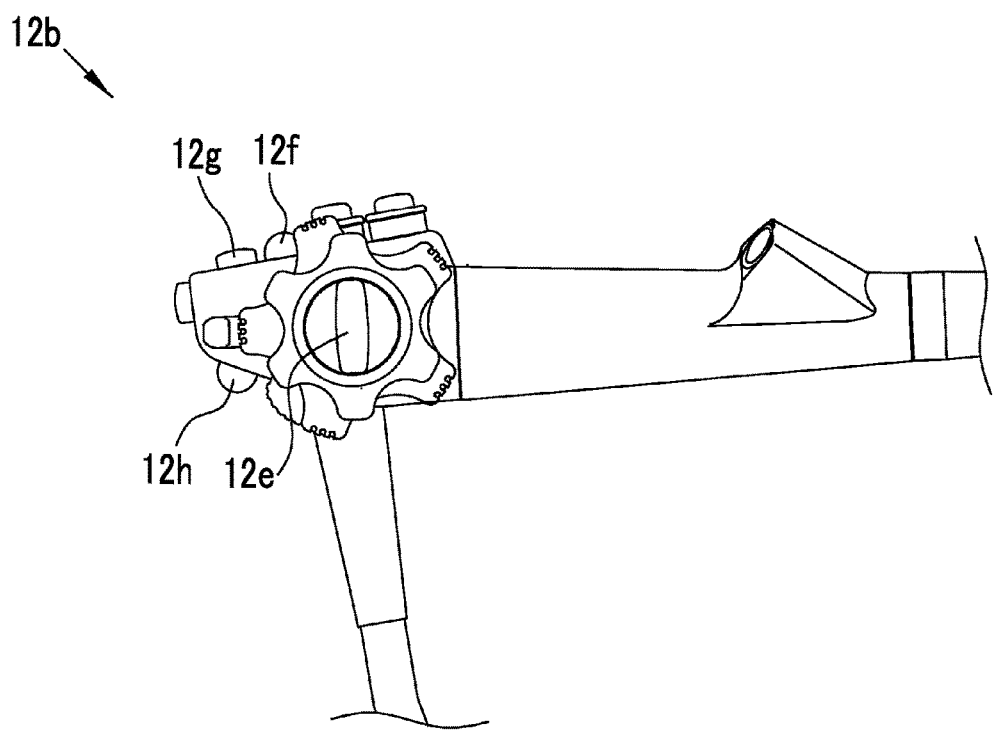
FIG. 2 is an external view of an operation part of an endoscope.

As shown in FIG. 2, the operation part 12b includes a mode changeover switch 12g that is used to perform an observation mode switching operation, a zoom operation portion 12h that is used to change an image pickup magnification, and a still image acquisition instruction portion 12f through which a still image acquisition instruction is given, in addition to the angle knob 12e. An operation or an instruction using a console 19, a foot switch (not shown), or the like, in addition to the mode changeover switch 12g or a scope switch of the still image acquisition instruction portion 12f, may be used for the observation mode switching operation, the zoom operation, or the still image acquisition instruction.

The endoscope system 10 has three modes, that is, a normal observation mode, a special observation mode, and a score display mode. In the normal observation mode, the observation target is illuminated with normal light and the image of the observation target is picked up, whereby a normal image having natural color tones is displayed on the display 18. In the special observation mode, the observation target is illuminated with special light having a wavelength range different from the wavelength range of normal light and the image of the observation target is picked up, whereby a special image in which a specific structure is enhanced is displayed on the display 18. In the score display mode, a score related to the determination of the severity or the stage of the disease of the observation target is decided on the basis of the endoscopic image consisting of the normal image or the special image, whereby, for example, the decided score, the change over time of the score, and/or the determination result is displayed on the display 18.

The severity of the disease is the degree of prognosis obtained by treatment, and is classified into three categories, that is, mild, moderate, and severe, for example, in a case where the disease is ulcerative colitis. The stage of the disease is classified into two categories, that is, an active stage and a remission stage in a case where the disease is ulcerative colitis. Therefore, the determination result of the severity is any one of mild, moderate, or severe, and the determination result of the stage is any one of the active stage or the remission stage, or any one of remission or non-remission. In addition, the score is display with which the severity or the stage of the disease of the observation target can be recognized, and is a numerical value, a sentence, or the like. In the present embodiment, a case where an image processing device determines the remission or the non-remission of ulcerative colitis will be described.

The processor device 16 to which the endoscope 12 is connected is an image processing device that executes the score display mode. The image processing device comprises a processor. In the image processing device, programs related to an image signal acquisition unit 51, a DSP 52, a noise reduction unit 53, a signal processing unit 55, a video signal generation unit 56, and the like are incorporated in a memory. The programs are operated by a control unit (not shown) formed of a processor, whereby functions such as the image signal acquisition unit 51, the DSP 52, the noise reduction unit 53, the signal processing unit 55, and the video signal generation unit 56 are realized. The score display mode may be executed in another configuration. For example, the functions of the image processing device may be provided in an external image processing system separated from the endoscope system 10, an external image processing device may receive the endoscopic image to execute the score display mode, and the execution result may be displayed on an external display connected to the external image processing system.

The processor device 16 is electrically connected to the display 18 and the console 19. The display 18 outputs and displays, for example, an image of the observation target, a score, a change over time of the score, a determination result, and/or information incidental to the image of the observation target. The console 19 functions as a user interface that receives an input operation, such as function settings. An external recording unit (not shown) that records images, image information, or the like may be connected to the processor device 16.

Figure 3:
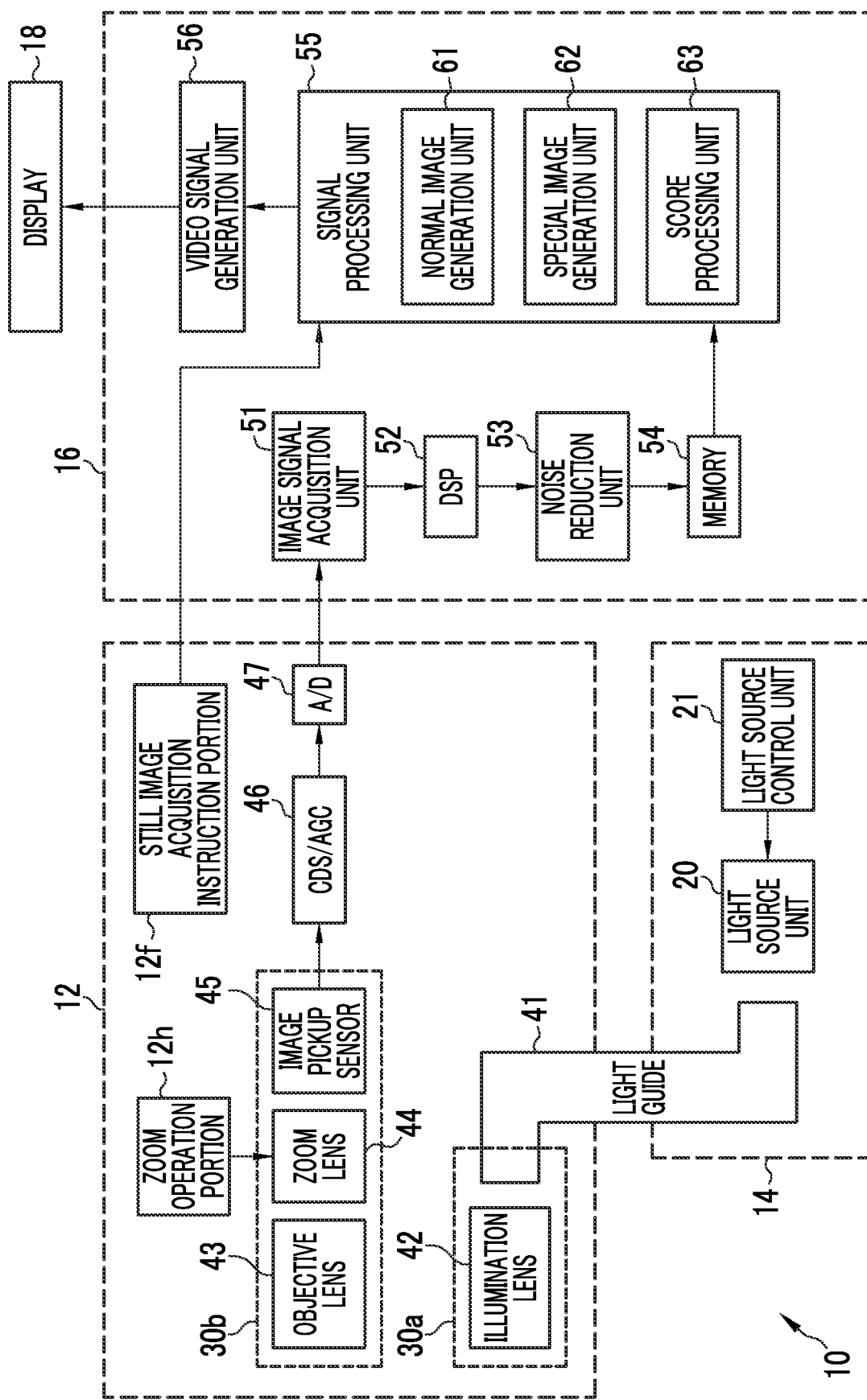
FIG. 3 is a block diagram showing a function of the endoscope system.

In FIG. 3, the light source device 14 emits illumination light with which the observation target is irradiated. The light source device 14 comprises a light source unit 20 and a light source control unit 21 that controls the light source unit 20. The light source unit 20 is formed of, for example, a semiconductor light source, such as a multi-color light emitting diode (LED), a combination of a laser diode and a phosphor, or a halogen light source, such as a xenon lamp. In addition, the light source unit 20 includes, for example, an optical filter that is used to adjust the wavelength range of light emitted by the LED or the like. The light source control unit 21 turns on/off each LED or the like or adjusts the drive current and drive voltage of each LED or the like, thereby controlling the amount of illumination light. Further, the light source control unit 21 controls the wavelength range of the illumination light by changing the optical filter or the like.

Figure 4:
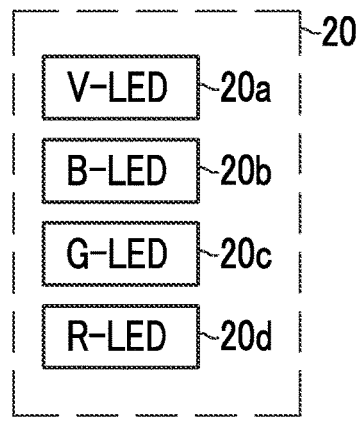
FIG. 4 is a diagram illustrating four-color LEDs provided in a light source unit.

As shown in FIG. 4, in the present embodiment, the light source unit 20 includes four-color LEDs, that is, a violet light emitting diode (V-LED) 20*a*, a blue light emitting diode (B-LED) 20*b*, a green light emitting diode (G-LED) 20*c*, and a red light emitting diode (R-LED) 20*d*.

Figure 5:
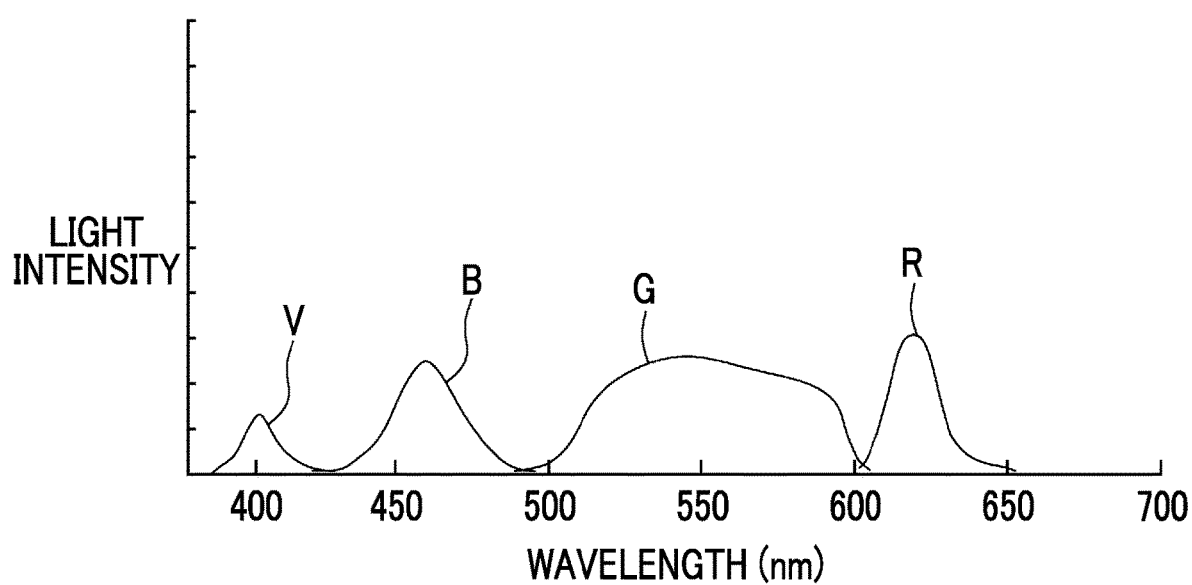
FIG. 5 is a graph showing spectra of violet light V, blue light B, green light G, and red light R.

As shown in FIG. 5, the V-LED 20*a* generates violet light V of which the central wavelength is 405±10 nm and the wavelength range is 380 to 420 nm. The B-LED 20*b* generates blue light B of which the central wavelength is 460±10 nm and the wavelength range is 420 to 500 nm. The G-LED 20*c* generates green light G of which the wavelength range is 480 to 600 nm. The R-LED 20*d* generates red light R of which the central wavelength is 620 to 630 nm and the wavelength range is 600 to 650 nm. Violet light V is short-wavelength light that is used to detect a superficial blood vessel dense part, an intramucosal hemorrhage part, or an extramucosal hemorrhage part, which is used in the score display mode, and preferably includes a central wavelength or a peak wavelength of 410 nm. Therefore, it is preferable that the endoscopic image used in the score display mode is an image obtained by picking up an image of the observation target illuminated with violet light V.

The light source control unit 21 controls the V-LED 20*a*, the B-LED 20*b*, the G-LED 20*c*, and the R-LED 20*d*. The light source control unit 21 controls the respective LEDs 20*a* to 20*d* so that normal light of which the light intensity ratios between violet light V, blue light B, green light G, and red light R are Vc:Bc:Gc:Rc is emitted in the normal observation mode.

Figure 6:
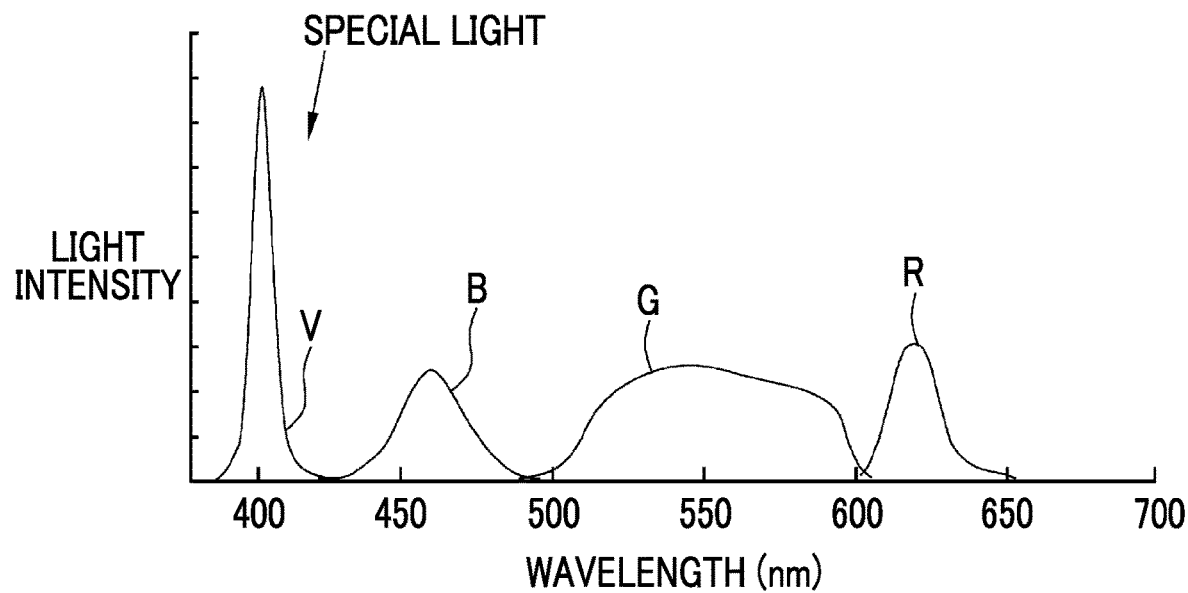
FIG. 6 is a graph showing spectra of special light.
Figure 7:
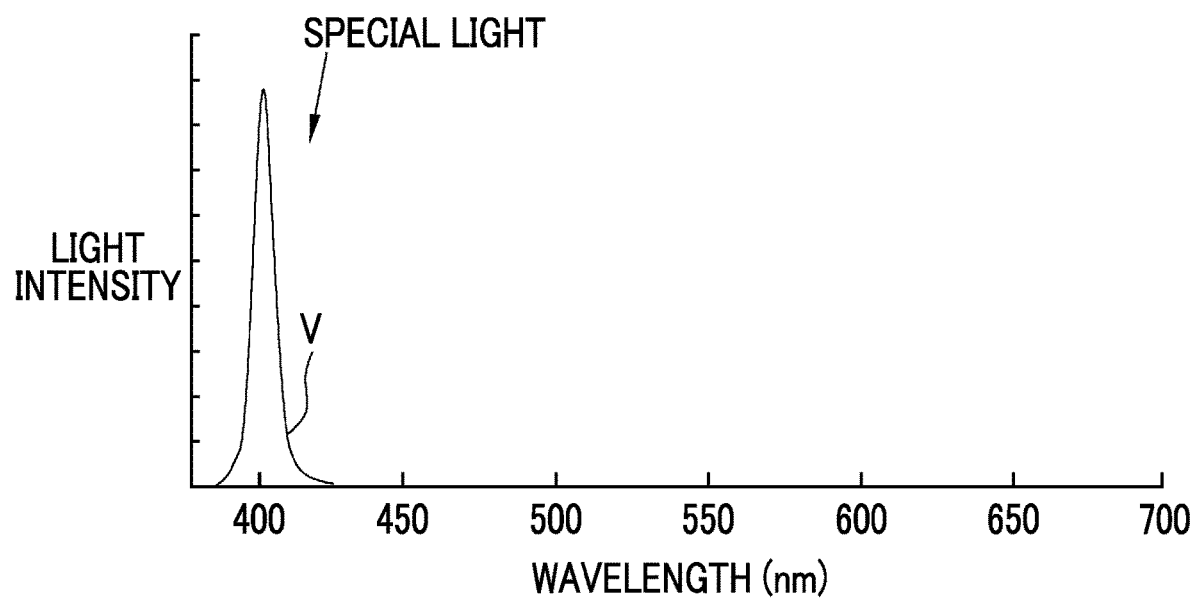
FIG. 7 is a graph showing a spectrum of special light including only violet light V.

The light source control unit 21 controls the respective LEDs 20*a* to 20*d* so that special light of which the light intensity ratios between violet light V as short-wavelength light, blue light B, green light G, and red light R are Vs:Bs:Gs:Rs is emitted in the special observation mode or the score display mode. It is preferable that special light enhances superficial blood vessels and the like. Therefore, it is preferable to make the light intensity of violet light V larger than the light intensity of blue light B, as the light intensity ratios Vs:Bs:Gs:Rs of the special light. For example, as shown in FIG. 6, a ratio of the light intensity Vs of violet light V to the light intensity Bs of blue light B is set to "4:1". Alternatively, as shown in FIG. 7, the light intensity ratios between violet light V, blue light B, green light G, and red light R are set to 1:0:0:0 and only violet light V as short-wavelength light may be emitted, for the special light.

It should be noted that the light intensity ratios include a case where the ratio of at least one semiconductor light source is 0 (zero), in the present specification. Therefore, the light intensity ratios include a case where any one or two or more of the semiconductor light sources are not turned on. The light source unit 20 is regarded to have light intensity ratios, for example, even in a case where only one semiconductor light source is turned on and the other three semiconductor light sources are not turned on as in a case where the light intensity ratios between violet light V, blue light B, green light G, and red light R are 1:0:0:0.

Light emitted from each of the LEDs 20*a* to 20*d* is incident on a light guide 41 through an optical path coupling unit (not shown) that is formed of a mirror, a lens, and the like. The light guide 41 is incorporated in the endoscope 12 and a universal cord (a cord that connects the endoscope 12 to the light source device 14 and the processor device 16). The light guide 41 propagates light from the optical path coupling unit to the distal end portion 12d of the endoscope 12.

The distal end portion 12d of the endoscope 12 is provided with an illumination optical system 30a and an image pickup optical system 30b. The illumination optical system 30a has an illumination lens 42, and the observation target is irradiated with illumination light propagated by the light guide 41, through the illumination lens 42. The image pickup optical system 30b has an objective lens 43, a zoom lens 44, and an image pickup sensor 45. Various types of light, such as light reflected from the observation target, scattered light, and fluorescence, are incident on the image pickup sensor 45 through the objective lens 43 and the zoom lens 44. With this, the image of the observation target is formed on the image pickup sensor 45. The zoom lens 44 freely moves between the telephoto end and the wide end with the operation of the zoom operation portion 12h, and magnifies and reduces the observation target of which the image is formed on the image pickup sensor 45.

The image pickup sensor 45 is a color image pickup sensor provided with any one of a red color (R) filter, a green color (G) filter, or a blue color (B) filter for each pixel, and picks up the image of the observation target to output image signals of respective RGB colors. A charge coupled device (CCD) image pickup sensor or a complementary metal-oxide semiconductor (CMOS) image pickup sensor can be used as the image pickup sensor 45. Further, a complementary color image pickup sensor provided with color filters of complementary colors, that is, cyan (C), magenta (M), yellow (Y), and green (G) may be used instead of the color image pickup sensor 45 provided with color filters of the primary colors. In a case where the complementary color image pickup sensor is used, the image signals of four colors of CMYG are output. Therefore, the same RGB image signals as those of the image pickup sensor 45 can be obtained by converting the image signals of the four colors of CMYG into the image signals of the three colors of RGB through the complementary color-primary color conversion. Alternatively, a monochrome image pickup sensor that is not provided with color filters may be used instead of the image pickup sensor 45.

The image pickup sensor 45 is driven and controlled by the image pickup control unit (not shown). The control performed by the image pickup control unit differs depending on the respective modes. In the normal observation mode or the score display mode, the image pickup control unit controls the image pickup sensor 45 to pick up the image of the observation target illuminated with normal light. With this, Bc image signals are output from the B pixels of the image pickup sensor 45, Gc image signals are output from the G pixels thereof, and Rc image signals are output from the R pixels thereof. In the special observation mode or the score display mode, the image pickup control unit controls the image pickup sensor 45 to pick up the image of the observation target illuminated with special light. With this, Bs image signals are output from the B pixels of the image pickup sensor 45, Gs image signals are output from the G pixels thereof, and Rs image signals are output from the R pixels thereof.

A correlated double sampling/automatic gain control (CDS/AGC) circuit 46 performs correlated double sampling (CDS) or automatic gain control (AGC) on analog image signals that are obtained from the image pickup sensor 45. The image signals that have been passed through the CDS/AGC circuit 46 are converted into digital image signals by an analog/digital (A/D) converter 48. The digital image signals that have been subjected to A/D conversion are input to the processor device 16.

The processor device 16 comprises the image signal acquisition unit 51, the digital signal processor (DSP) 52, the noise reduction unit 53, a memory 54, the signal processing unit 55, and the video signal generation unit 56. The signal processing unit 55 comprises a normal image generation unit 61, a special image generation unit 62, and a score processing unit 63.

The image signal acquisition unit 51 acquires the digital image signals of an endoscopic image, which are input from the endoscope 12. The acquired image signals are transmitted to the DSP 52. The DSP 52 performs various types of signal processing, such as defect correction processing, offset processing, gain correction processing, linear matrix processing, gamma conversion processing, demosaicing processing, and YC conversion processing, on the received image signals. In the defect correction processing, signals of defective pixels of the image pickup sensor 45 are corrected. In the offset processing, dark current components are removed from the image signals that have been subjected to the defect correction processing, and an accurate zero level is set. In the gain correction processing, the image signals of each color, which have been subjected to the offset processing, are multiplied by a specific gain, whereby the signal level of each image signal is adjusted.

The linear matrix processing for improving color reproducibility is performed on the image signals of each color, which have been subjected to the gain correction processing. After that, the brightness or chroma saturation of each image signal is adjusted through the gamma conversion processing. The demosaicing processing (also referred to as equalization processing or demosaicing) is performed on the image signals that have been subjected to the gamma conversion processing, and signals of lacking color in each pixel are generated by interpolation. All the pixels are made to have signals of the respective RGB colors through the demosaicing processing. The DSP 52 performs the YC conversion processing on each image signal that has been subjected to the demosaicing processing, and outputs brightness signals Y, color difference signals Cb, and color difference signals Cr to the noise reduction unit 53.

The noise reduction unit 53 performs noise reduction processing, which is performed through, for example, a moving average method or median filtering method, on the image signals that have been subjected to the demosaicing processing and the like by the DSP 52. The image signal with reduced noise is stored in the memory 54.

The signal processing unit 55 acquires the image signals that have been subjected to noise reduction, from the memory 54. Then, signal processing, such as color conversion processing, hue enhancement processing, and structure enhancement processing, is performed as necessary on the acquired image signals, and a color endoscopic image in which the observation target is imaged is generated. The color conversion processing is processing for performing color conversion through 3×3 matrix processing, gradation transformation processing, three-dimensional lookup table (LUT) processing, and the like on the image signals. The hue enhancement processing is performed on the image signals that have been subjected to the color conversion processing. The structure enhancement processing is processing for enhancing, for example, a specific tissue or structure included in the observation target, such as blood vessels or pit patterns, and is performed on the image signals that have been subjected to the hue enhancement processing.

The signal processing unit 55 comprises the normal image generation unit 61, the special image generation unit 62, and the score processing unit 63. The signal processing unit 55 sets a destination to which the image signals from the noise reduction unit 53 are transmitted to any one of the normal image generation unit 61, the special image generation unit 62, or the score processing unit 63, in response to the set mode. Specifically, the image signals are input to the normal image generation unit 61, for example, in a case where the normal observation mode is set. The image signals are input to the special image generation unit 62 in a case where the special observation mode is set. The image signals are input to the score processing unit 63 in a case where the score display mode is set.

The normal image generation unit 61 performs image processing for a normal image on the input Rc image signals, Gc image signals, and Bc image signals corresponding to one frame. The image processing for a normal image includes color conversion processing, such as 3×3 matrix processing, gradation transformation processing, and three-dimensional look up table (LUT) processing, hue enhancement processing, and structure enhancement processing, such as spatial frequency enhancement. The Rc image signals, the Gc image signals, and the Bc image signals that have been subjected to the image processing for a normal image are input to the video signal generation unit 56 as a normal image.

The special image generation unit 62 performs image processing for a special image on the input Rs image signals, Gs image signals, and Bs image signals corresponding to one frame. The image processing for a special image includes color conversion processing, such as 3×3 matrix processing, gradation transformation processing, and three-dimensional LUT processing, hue enhancement processing, and structure enhancement processing, such as spatial frequency enhancement. The Rs image signals, the Gs image signals, and the Bs image signals that have been subjected to the image processing for a special image are input to the video signal generation unit 56 as a special image.

Since the endoscopic image generated by the signal processing unit 55 is a normal observation image in a case where the observation mode is the normal observation mode, and is a special observation image in a case where the observation mode is the special observation mode, the contents of the color conversion processing, the hue enhancement processing, and the structure enhancement processing differ depending on the observation modes. In the normal observation mode, the signal processing unit 55 generates the normal observation image by performing the various types of signal processing for making the observation target have natural color tones. In the special observation mode, the signal processing unit 55 generates the special observation image by performing the above various types of signal processing for enhancing at least the blood vessels of the observation target. In the special observation image generated by the signal processing unit 55, blood vessels (so-called superficial blood vessels) or blood located at a relatively shallow position in the observation target with respect to the surface of the mucous membrane have magenta-based color (for example, brown color), and blood vessels located at a relatively deep position in the observation target with respect to the surface of the mucous membrane (so-called medium-deep blood vessels) have cyan-based color (for example, green color). Therefore, the blood vessels or hemorrhage (blood) of the observation target is enhanced by a difference in color with respect to the mucous membrane represented by pink-based color.

The video signal generation unit 56 converts the normal image and the special image that are output from the signal processing unit 55, a final score decided by the score processing unit 63, or the like into video signals allowing full-color display on the display 18. The video signals that have been converted are input to the display 18. With this, the normal image, the special image, the final score, or the like is displayed on the display 18. Further, in a case where a still image acquisition instruction (freeze instruction or release instruction) is input by the operation of the still image acquisition instruction portion 12*f*, the signal processing unit 55 stores the generated endoscopic image in an image storage unit 75 (see FIG. 8) or a storage (not shown). The storage is an external storage device connected to the processor device 16 through a local area network (LAN) or the like, and is, for example, a file server of a system for filing an endoscopic image, such as a picture archiving and communication system (PACS, see FIG. 21), or a network attached storage (NAS).

Figure 8:
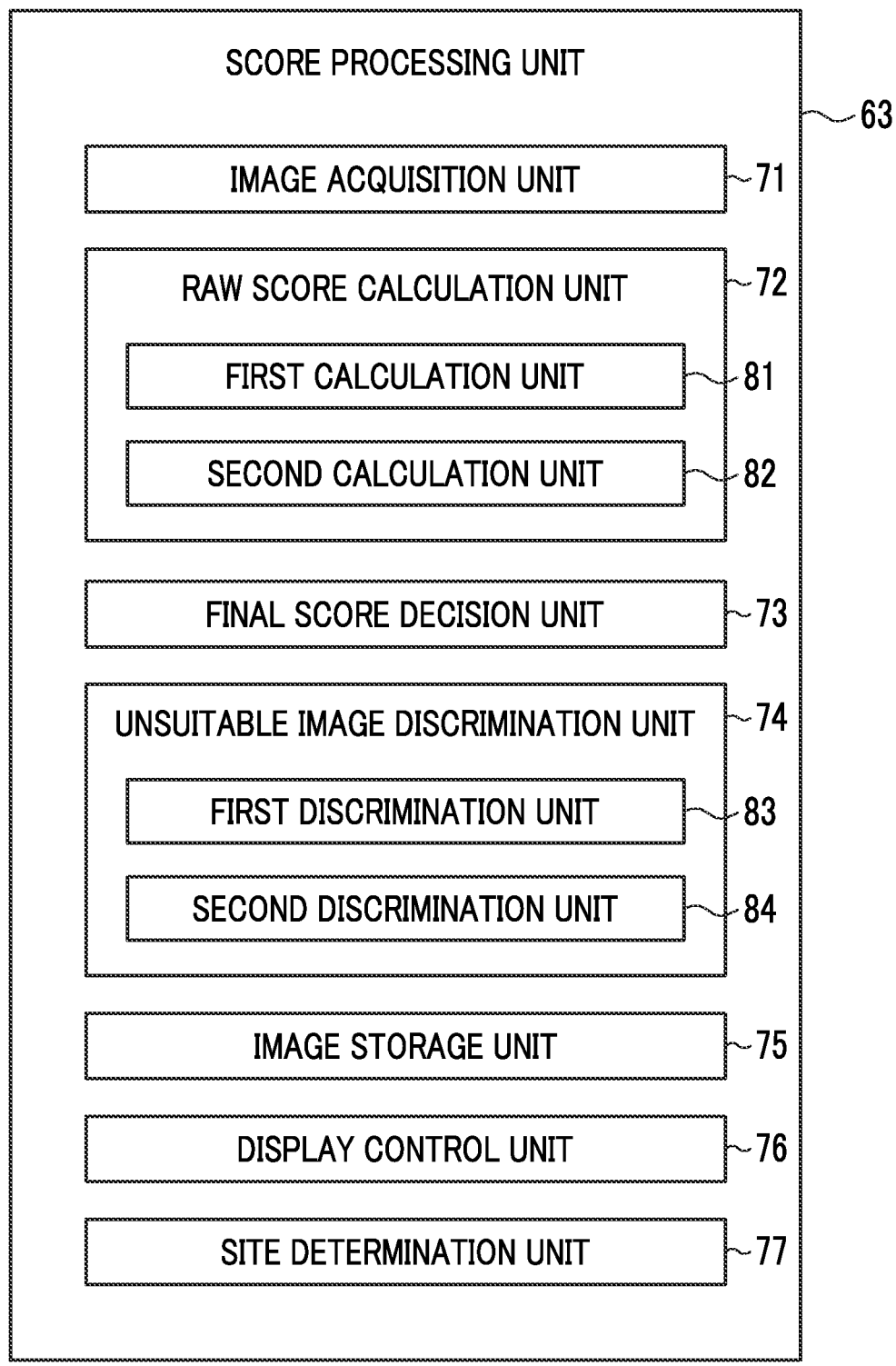
FIG. 8 is a block diagram showing a function of a score processing unit.

The score processing unit 63 decides the final score, and performs control to display the final score and/or the change over time of the final score in real time on the display 18. As shown in FIG. 8, the score processing unit 63 comprises an image acquisition unit 71, a raw score calculation unit 72, a final score decision unit 73, and a display control unit 76. Further, an unsuitable image discrimination unit 74, the image storage unit 75, and a site determination unit 77 may be provided.

In the score display mode, the image acquisition unit 71 automatically acquires a plurality of endoscopic images obtained by picking up images of the observation target with the endoscope 12 at times different from each other. Although the endoscopic images include the normal observation image and the special observation image, the image acquisition unit 71 acquires a special observation image in which blood vessels and the like are enhanced, in the present embodiment. The image acquisition unit 71 may acquire the endoscopic image from the storage in some cases. The endoscopic image acquired by the image acquisition unit 71 is sent to the raw score calculation unit 72, the unsuitable image discrimination unit 74, or the image storage unit 75.

The raw score calculation unit 72 calculates a raw score related to the determination of the severity or the stage of the disease of the observation target on the basis of the plurality of endoscopic images acquired by the image acquisition unit 71. The raw score related to the determination of the severity or the stage of the disease of the observation target is set to a numerical value with which the severity or the stage of the disease of the observation target included in the endoscopic image can be recognized. The raw score calculation unit 72 can be provided with one or both of a first calculation unit 81 (see FIG. 8) and a second calculation unit 82 (see FIG. 8).

It is preferable that the raw score calculation unit 72 calculates the raw score on the basis of a feature amount (first feature amount) obtained by analyzing the endoscopic image, through the first calculation unit 81. Examples of the feature amount include a feature amount related to the blood vessels, such as the number, thicknesses, lengths, number of branches, branch angles, distance between branch points, number of intersections, inclination, density, color, blood concentration, oxygen saturation, presence/absence of hemorrhage, area of hemorrhage or flow rate of blood vessels, or a feature amount related to the color of the mucous membrane.

Examples of the feature amount of the raw score related to the severity or the stage of ulcerative colitis preferably include the amount related to the superficial blood vessel dense part, the intramucosal hemorrhage part, and the extramucosal hemorrhage part included in the endoscopic image. For the superficial blood vessel dense part, blood vessels of the observation target are extracted from the endoscopic image by a frequency filter or the like through the image analysis on the endoscopic image, and a value obtained by counting the number of pixels of a part where blood vessels are dense in the endoscopic image is set to the raw score. Similarly, for the intramucosal or extramucosal hemorrhage part, the intramucosal or extramucosal hemorrhage of the observation target is extracted from the endoscopic image with a value of a G value with respect to an R value proportional to the amount of hemoglobin or the like, and a value obtained by counting the number of pixels of the intramucosal or extramucosal hemorrhage part in the endoscopic image is set to the raw score.

Figure 9:
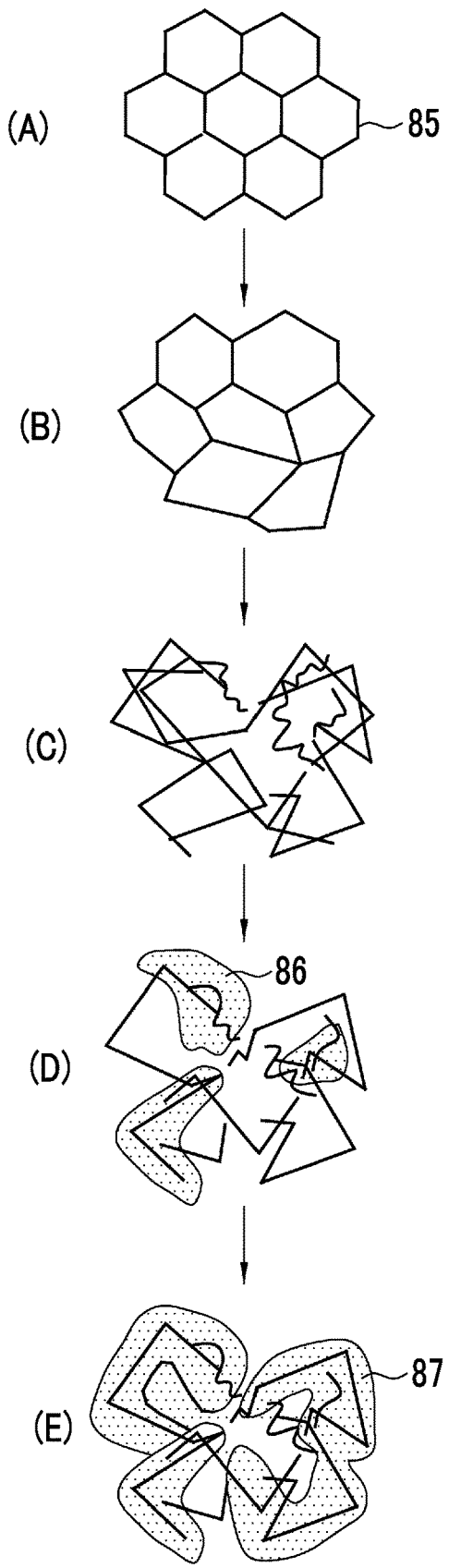
FIG. 9 is a view illustrating a pattern of a blood vessel structure that varies depending on a severity of ulcerative colitis.

The following method can also be used as a method of counting the number of pixels of the superficial blood vessel dense part, the intramucosal hemorrhage part, and the extramucosal hemorrhage part included in the endoscopic image. First, the present inventor has found out that ulcerative colitis, which is a disease to be determined by the present embodiment, changes the pattern of a blood vessel structure as the severity is exacerbated, as shown in (A) to (E) of FIG. 9. In a case where ulcerative colitis has remitted or ulcerative colitis has not occurred, the patterns of superficial blood vessels 85 are regular ((A) of FIG. 9) or the regularity of the patterns of the superficial blood vessels 85 is slightly disturbed ((B) of FIG. 9). On the other hand, in a case where ulcerative colitis has not remitted and the severity of ulcerative colitis is mild, the superficial blood vessels 85 are dense ((C) of FIG. 9). Alternatively, in a case where ulcerative colitis has not remitted and the severity of ulcerative colitis is moderate, intramucosal hemorrhage 86 occurs ((D) of FIG. 9). Alternatively, in a case where ulcerative colitis has not remitted and the severity of ulcerative colitis is moderate to severe, extramucosal hemorrhage 87 occurs ((E) of FIG. 9). The raw score calculation unit 72 can calculate the raw score by using the above pattern change of the blood vessel structure.

Figure 10:
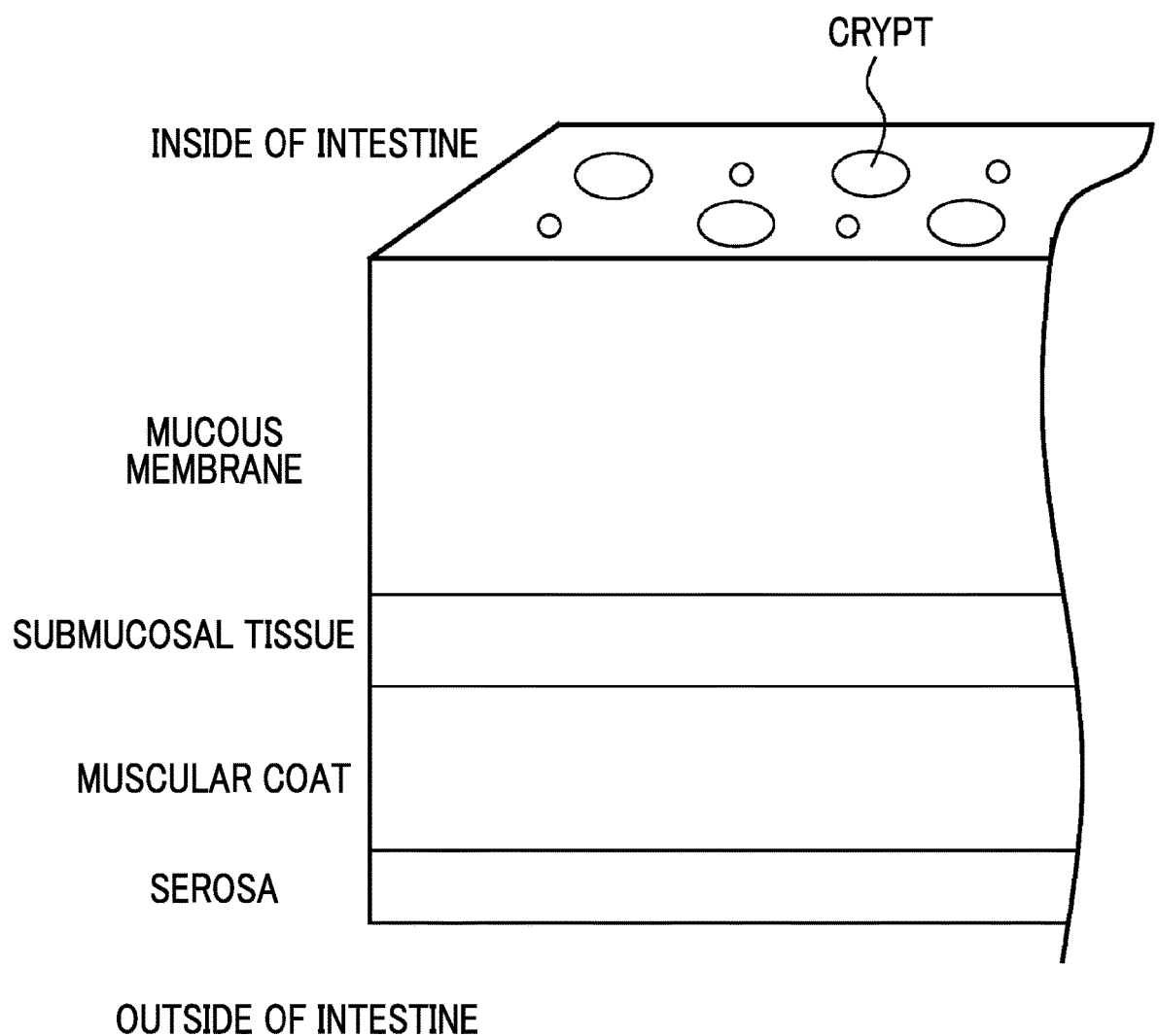
FIG. 10 is a schematic view schematically showing a cross-section of a large intestine.

Here, the superficial blood vessel dense part refers to a state in which superficial blood vessels meander and gather, and refers to a part in which many superficial blood vessels surround the crypt (see FIG. 10) in terms of appearance on the image. The intramucosal hemorrhage refers to hemorrhage within the mucous membrane (see FIG. 10) and requires to be discriminated from hemorrhage into the inner cavity. The intramucosal hemorrhage refers to hemorrhage in the mucous membrane, not the inner cavity (the lumen, a hole having plicae) in terms of appearance on the image. The extramucosal hemorrhage refers to a small amount of blood that flows into the lumen, blood that oozes out of the lumen or the mucous membrane located in front of the endoscope even after the inside of the lumen has been washed and that can be visually recognized, or intraluminal blood with bleeding on a hemorrhagic mucous membrane.

Figure 11:
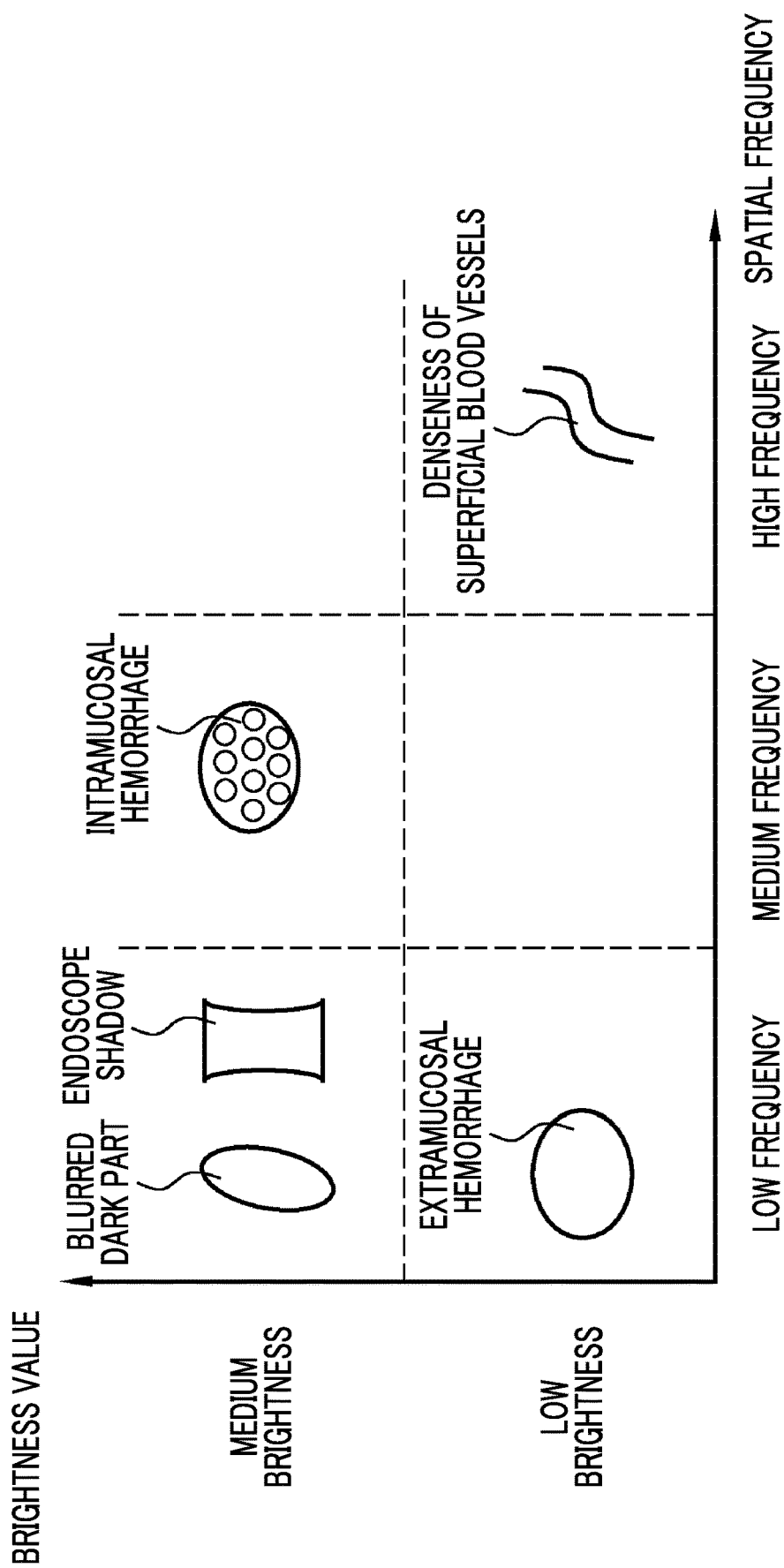
FIG. 11 is a diagram illustrating that a superficial blood vessel dense part, an intramucosal hemorrhage part, and an extramucosal hemorrhage part are classified by brightness values and spatial frequencies.

The raw score calculation unit 72 classifies the superficial blood vessel dense part, the intramucosal hemorrhage part, or the extramucosal hemorrhage part according to the frequency characteristic and the brightness value obtained from the special observation image. Specifically, the superficial blood vessel dense part, the intramucosal hemorrhage part, or the extramucosal hemorrhage part are classified as shown in FIG. 11. The denseness of superficial blood vessels is represented by a low brightness value and a high frequency characteristic. The intramucosal hemorrhage is represented by a medium brightness value and a medium frequency characteristic. The extramucosal hemorrhage is represented by a low brightness value and a low frequency characteristic. In a case where various structures of the special observation image are represented by brightness values and frequency characteristics, a blurred dark part, an endoscope shadow (a shadow that can be generated at the central part of an endoscopic image in a case where the distal end portion 12d of the endoscope is moved along the lumen), or the like of the special observation image is also included, in addition to the above-described three, that is, the superficial blood vessel dense part, the intramucosal hemorrhage part, and the extramucosal hemorrhage part. The denseness of superficial blood vessels, the intramucosal hemorrhage, and the extramucosal hemorrhage that are necessary for the determination of the remission or the non-remission of ulcerative colitis are extracted from the superficial blood vessel dense part, the intramucosal hemorrhage part, or the extramucosal hemorrhage part by using the above-described classification.

For the spatial frequency, the spatial frequency component distribution is calculated by applying Laplacian filter to the special observation image. For example, in a case where the standard deviation of the frequencies of nine pixels that are disposed near a part including a specific pixel is a constant value or less, the specific pixel is defined as a pixel belonging to a low frequency region on the basis of the spatial frequency component distribution. A high frequency region is extracted by Hessian analysis for the spatial frequency component distribution. A medium frequency region is a medium frequency region corresponding to a part in which the low frequency region and the high frequency region are excluded from the special observation image. In this way, it is possible to calculate the number of pixels of the superficial blood vessel dense part, the intramucosal hemorrhage part, or the extramucosal hemorrhage part by classifying the pixels of the special observation image by using the spatial frequency and the brightness value. As described above, it is preferable that the disease is ulcerative colitis because the determination of the severity or the stage of the disease can be satisfactorily performed with the above configuration.

The raw score calculated on the basis of a different first feature amount is used as a different type of raw score. The raw score calculation unit 72 may calculate one type of raw score or two or more types of raw scores.

The raw score calculation unit 72 calculates the raw score on the basis of the endoscopic image, through the second calculation unit 82. The second calculation unit 82 comprises a trained first machine learning model. The trained first machine learning model is generated by an input of the past endoscopic image associated with the raw score to a machine learning model. That is, the trained first machine learning model is a machine learning model generated by causing the machine learning model to learn to correctly output the associated raw score in response to an input of the past endoscopic image to the machine learning model. Therefore, the "trained" includes the adjustment of various parameters in addition to the input of the past endoscopic image associated with the score to the machine learning model. For example, a numerical value obtained by quantifying the severity or the stage of the disease of the observation target, or a feature amount may be used as the raw score associated with the past endoscopic image. For example, the first machine learning model may be provided with two or more types of machine learning models corresponding to the respective feature amounts, and may calculate two or more types of raw scores.

The final score decision unit 73 decides the final score on the basis of the raw score. The raw score calculated by the raw score calculation unit 72 is an amount related to the determination of the severity or the stage of the disease, and is an indicator of how symptomatic the disease is or how advanced the disease is. Therefore, the method of deciding the final score may be adjusted according to the purpose of the determination and the like. For example, in a case where the degree of the severity or the progress of the stage is determined, the final score is set in terms of a large raw score value, a high severity, and an advanced stage, and the severity or the stage is determined for a part where the disease is most exacerbated. In this case, examples of the method of deciding the final score include a method of setting the respective threshold values in advance for three types of raw scores, that is, the number of pixels of the superficial blood vessel dense part, the number of pixels of the intramucosal hemorrhage part, and the number of pixels of the extramucosal hemorrhage part, to decide a raw score exceeding the threshold value as the final score, or to decide a raw score having a largest excess of the preset threshold value in terms of a high raw value, among the respective values of the three types of raw scores, as the final score. On the other hand, for example, in a case of screening, the threshold value is set low.

The display control unit 76 performs control to display the final score and/or the change over time of the final score in real time on the display 18. Examples of the method of displaying the final score include a method of displaying the numerical value of the final score value in real time on the display 18, a method of displaying the numerical value of the final score value in a graph format as the change over time of the final score with a graph of which the vertical axis is the final score value and the horizontal axis is the passage of time, or a method of displaying the final score value and the preset threshold value by using a message for giving notice of the determination result of the severity or the stage of the disease. Further, the display control unit 76 also performs control not to display the final score or the like. For example, in a case where the final score is smaller than the preset threshold value, the final score is not displayed. It should be noted that displaying in real time means displaying immediately, and does not mean displaying at exactly the same time.

In a case where the position to be imaged is changed and the observation target is changed, the obtained endoscopic image is also changed, and the raw score calculated on the basis of the endoscopic image is also changed. However, the change in the raw score is not displayed as it is on the display 18, and a final score using the raw score is decided as the final score because the score processing unit 63 configured as described above decides the final score by using the raw score and then displays the decided final score on the display 18, so that a more stable score is displayed on the display 18 even in real time. Further, since control not to display the final score is performed depending on the final score value, a more stable score is displayed in a case where the score is displayed. In addition, the change over time of the final score is displayed in real time, so that it is possible to grasp at a glance, for example, the change of the severity or the stage because of the change of the position to be imaged or how high the final score is at the position where the severity is highest or the stage is the most advanced in a case where the position to be imaged is changed and the observation target is changed, in one observation. Therefore, the user can grasp the part where the severity, the stage of the disease, or the like in the course of the observation is the worst while concentrating on the observation. As described above, with the image processing device, the final score does not vary even in a case where the observation target is finely changed, and more stable and robust score calculation and display of the final score or the like are performed. Accordingly, the image processing device contributes to the prevention of oversight of the lesion of the user who performs the observation or to the simpler observation.

The score processing unit 63 may be provided with the unsuitable image discrimination unit 74. The unsuitable image discrimination unit 74 discriminates whether the endoscopic image is suitable or unsuitable for the calculation of the raw score. Whether the endoscopic image is suitable or unsuitable is discriminated through the discrimination. The endoscopic image may be unsuitable as an image for calculating the raw score. An extreme numerical value may be calculated in a case where the raw score is calculated, for example, for reasons such as that the observation target is blurred because imaging is performed while the distal end portion 12d of the endoscope is moving, that the observation target is out of focus because water droplets are attached, that many blurred parts are generated because the observation target is diagonally positioned, or that the observation target is hardly included because only the distant view is imaged, in the endoscopic image. Such endoscopic images in which there is a concern that inappropriate scores may be calculated are discriminated to be unsuitable for the calculation of the raw score. The score processing unit 63 can be provided with one or both of a first discrimination unit 83 (see FIG. 8) and a second discrimination unit 84 (see FIG. 8).

The first discrimination unit 83 discriminates whether the endoscopic image is suitable or unsuitable for the calculation of the raw score, on the basis of the feature amount (second feature amount) obtained by analyzing the endoscopic image. It is preferable that an amount related to at least one selected from halation distribution, spatial frequency distribution, brightness value distribution, shadow distribution, a magnification ratio indicator, and reflected light distribution of illumination light emitted to the observation target of the endoscopic image is used as the feature amount in this case.

In the endoscopic image, since a region where halation occurs or a region of shadow generated due to the hood or the like of the endoscope is an extremely bright or dark region, the endoscopic image having a large number of these regions is unsuitable for the calculation of the raw score. An endoscopic image having a large number of extremely bright or dark regions due to the brightness value distribution or the shadow distribution is also unsuitable for the calculation of the raw score. An endoscopic image having a large number of regions where the image is blurred due to the spatial frequency distribution is unsuitable for the calculation of the raw score because the image is blurred or out of focus. In addition, in a case where a magnification ratio is large when a magnification ratio indicator is referred to, the imaged appearance of blood vessels is changed and the blood vessel density per unit area is changed, for example, in a case where the superficial blood vessel dense part is calculated, as compared with a case where no magnification occurs. Therefore, a case where the raw score is calculated in consideration of the magnification ratio is suitable, and a case where the magnification ratio is not considered is unsuitable for the calculation of the raw score. Further, in a case where the observation target is changed to a different type because of the change of an observation site or the like, the reflected light distribution of illumination light emitted to the observation target may be changed. An endoscopic image having a large number of extremely bright or dark regions due to the change of the reflected light distribution is also unsuitable for the calculation of the raw score.

Further, the value calculated on the basis of a different second feature amount is used as a different type of second feature amount. The first discrimination unit 83 may calculate one type or two or more types of second feature amounts. The first discrimination unit 83 discriminates whether the endoscopic image is suitable or unsuitable for the calculation of the raw score by using one type or two or more types of second feature amounts.

The unsuitable image discrimination unit 74 discriminates whether the endoscopic image is suitable or unsuitable for the calculation of the raw score on the basis of the endoscopic image, through the second discrimination unit 84. The second discrimination unit 84 comprises a trained second machine learning model. The trained second machine learning model is generated by an input of the past endoscopic image associated with whether the endoscopic image is suitable or unsuitable for the calculation of the raw score, to a machine learning model. That is, the trained second machine learning model is a machine learning model generated by causing the machine learning model to learn to correctly output whether the endoscopic image is suitable or unsuitable for the calculation of the raw score, in response to an input of the past endoscopic image to the machine learning model. Therefore, the "trained" includes the adjustment of various parameters in addition to the input of the past endoscopic image associated with whether the endoscopic image is suitable or unsuitable for the calculation of the raw score, to the machine learning model.

An endoscopic image discriminated to be suitable for the calculation of the raw score by the unsuitable image discrimination unit 74 is sent to the raw score calculation unit 72, and the raw score is calculated. The raw score is defined to be "uncalculated" for an endoscopic image discriminated to be unsuitable for the calculation of the raw score. That is, since the raw score is labeled as "uncalculated", the endoscopic image for which the raw score is defined to be uncalculated is distinguished from the endoscopic image for which the raw score has not been calculated yet.

Figure 12:
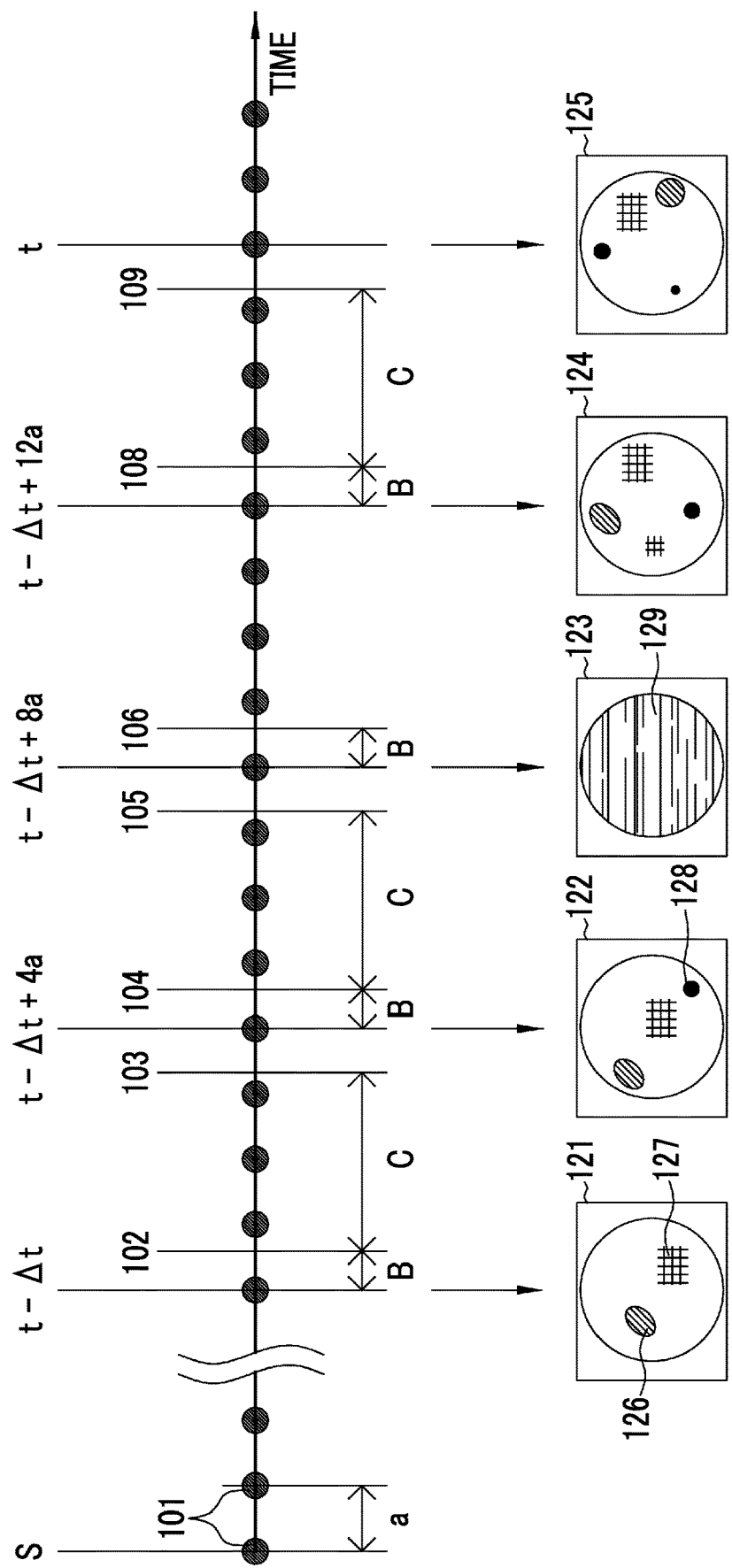
FIG. 12 is a diagram illustrating relation between an endoscopic image and raw score calculation in time series.

It is preferable that the final score decision unit 73 decides the final score from the raw score that is calculated on the basis of the plurality of endoscopic images acquired in a predetermined period before a point in time at which the final score is decided. The decision of the final score in this case will be described in detail with reference to FIG. 12. In FIG. 12, the flow from the observation start through the endoscope is shown in the upper part, and the appearance of the obtained endoscopic image is shown in the lower part. Observation through the endoscope is started, and endoscopic image acquisition 101 is started from observation start time S. The image signal acquisition unit 51 automatically performs the endoscopic image acquisition 101 at a predetermined image acquisition interval a. As soon as the endoscopic image acquisition 101 is performed, the raw score of the endoscopic image is calculated. Unsuitable image discrimination may be performed prior to the calculation. In FIG. 12, although the endoscopic image acquisition 101 is indicated by a filled circle, only a part thereof is marked in order to avoid complicating the figure. Further, also for the image acquisition interval a, only a part thereof is marked in order to avoid complicating the figure. The final score is decided on the basis of the endoscopic image acquired in a period Δt before final score decision time t, which is the decision time of the final score. The period Δt is a predetermined period and is set in advance.

A first endoscopic image acquired in the period Δt is an endoscopic image 121 acquired at time t−Δt. The endoscopic image 121 includes an intramucosal hemorrhage part 126 and a blood vessel dense part 127. In FIG. 12, although the intramucosal hemorrhage part 126 and the blood vessel dense part 127 are shown by a diagonally hatched portion and a cross hatched portion, respectively, only a part thereof is marked in order to avoid complicating the figure. The unsuitable image discrimination unit 74 uses a period B to discriminate whether the endoscopic image 121 obtained by the endoscopic image acquisition 101 at time t−Δt is suitable or unsuitable for the calculation of the raw score, and obtains the discrimination result at the time of unsuitable image discrimination 102. The discrimination result is "suitable".

The raw score calculation unit 72 uses a period C to calculate the raw score in the endoscopic image 121 after the unsuitable image discrimination 102, and obtains the calculation result at the time of raw score calculation 103. The raw score calculation unit calculates the raw scores through the first calculation unit 81 for two types, that is, the number of pixels of the intramucosal and extramucosal hemorrhage parts (hereinafter, referred to as the number of pixels of a hemorrhage part) and the number of pixels of the blood vessel dense part (hereinafter, referred to as the number of pixels of a dense part). The calculation results are "the number of pixels of the hemorrhage part: 100" and "the number of pixels of the dense part: 70".

Next, among the endoscopic images acquired in the period Δt, a second raw score is calculated for an endoscopic image 122 acquired at time t−Δt+4a. The endoscopic image 122 includes the intramucosal hemorrhage part 126, the blood vessel dense part 127, and an extramucosal hemorrhage part 128. In FIG. 12, although the extramucosal hemorrhage part 128 is indicated by a filled circle, only a part thereof is marked in order to avoid complicating the figure. The unsuitable image discrimination unit 74 uses the period B to discriminate whether the endoscopic image 122 obtained by the endoscopic image acquisition 101 at time t−Δt+4a is suitable or unsuitable for the calculation of the raw score, and obtains the discrimination result at the time of unsuitable image discrimination 104. The discrimination result is "suitable".

The raw score calculation unit 72 uses the period C to calculate the raw score in the endoscopic image 122 after the unsuitable image discrimination 104, and obtains the calculation result at the time of raw score calculation 105. The raw score calculation unit calculates the raw scores through the first calculation unit 81 for two types, that is, the number of pixels of the hemorrhage part and the number of pixels of the dense part. The calculation results are "the number of pixels of the hemorrhage part: 120" and "the number of pixels of the dense part: 90".

Next, among the endoscopic images acquired in the period Δt, a third raw score is calculated for an endoscopic image 123 acquired at time t−Δt+8a. Since the endoscopic image 123 is acquired while the endoscope is moving, the endoscopic image 123 is an unclear image 129 in which the observation target is blurred, and the observation target cannot be discriminated. The unsuitable image discrimination unit 74 uses the period B to discriminate whether the endoscopic image 123 obtained by the endoscopic image acquisition 101 at time t−Δt+8a is suitable or unsuitable for the calculation of the raw score, and obtains the discrimination result at the time of unsuitable image discrimination 106. The discrimination result is "unsuitable".

The raw score calculation unit 72 receives that the result of the unsuitable image discrimination is "unsuitable" after the unsuitable image discrimination 106, and does not calculate the raw score. That is, the calculation result of the raw score is defined to be "uncalculated".

Next, among the endoscopic images acquired in the period Δt, a fourth raw score is calculated for an endoscopic image 124 acquired at time t–Δt+12a. The endoscopic image 124 includes the intramucosal hemorrhage part 126, the blood vessel dense part 127, and the extramucosal hemorrhage part 128. The unsuitable image discrimination unit 74 uses the period B to discriminate whether the endoscopic image 124 obtained in the endoscopic image acquisition 101 at time t–Δt+12a is suitable or unsuitable for the calculation of the raw score, and obtains the discrimination result at the time of unsuitable image discrimination 108. The discrimination result is "suitable".

The raw score calculation unit 72 uses the period C to calculate the raw score in the endoscopic image 124 after the unsuitable image discrimination 108, and obtains the calculation result at the time of raw score calculation 109. The raw score calculation unit calculates the raw scores through the first calculation unit 81 for two types, that is, the number of pixels of the hemorrhage part and the number of pixels of the dense part. The calculation results are "the number of pixels of the hemorrhage part: 140" and "the number of pixels of the dense part: 140".

In this way, the endoscopic images acquired in the period Δt are the four endoscopic images 121, 122, 123, and 124 in relation to the image acquisition interval a, the period of the unsuitable image discrimination performed by the unsuitable image discrimination unit 74, the period of the raw score calculation performed by the raw score calculation unit 72. It is preferable that the final score decision unit 73 decides the final score on the basis of the raw scores except for the raw score to be "uncalculated", among these endoscopic images. Therefore, the final score decision unit 73 decides the final score from the respective raw scores calculated on the basis of the three endoscopic images 121, 122, and 124.

It is preferable that the final score decision unit 73 decides the final score by performing a moving average, or finite impulse response (FIR) filtering or infinite impulse response (IIR) filtering of the plurality of raw scores. The moving average is preferably any one of a simple moving average, a weighted moving average, an exponential moving average, or a triangular moving average. In a case where weighting is used in the moving average, a value decided so as to obtain a preferable result can be set in advance and used according to the observation site, a difference in the conditions for acquiring the endoscopic image, and the like. The moving average, or FIR filtering or IIR filtering is used, so that it is possible to decide the final score, for example, with less influence of noise, such as raw scores of extremely distant values, in a plurality of raw scores. Accordingly, the final score is stably decided.

In a case where the final score is determined by using, for example, a simple moving average of the raw scores at the final score decision time t, the numbers of pixels of the hemorrhage part in the endoscopic images 121, 122, and 124 are averaged when the raw score is for the number of pixels of the hemorrhage part. That is, for the first type of the final score, the number of pixels 100 of the hemorrhage part of the endoscopic image 121, the number of pixels 120 of the hemorrhage part of the endoscopic image 122, and the number of pixels 140 of the hemorrhage part of the endoscopic image 124 are averaged to 120 as in Equation (1). Similarly, for the second type of the final score, the number of pixels 70 of the dense part of the endoscopic image 121, the number of pixels 90 of the dense part of the endoscopic image 122, and the number of pixels 140 of the dense part of the endoscopic image 124 are averaged to 100 as in Equation (2).

$$\text{Final score (the number of pixels of the hemorrhage part)} = (100+120+140)/3 = 120 \quad (1)$$

$$\text{Final score (the number of pixels of the dense part)} = (70+90+140)/3 = 100 \quad (2)$$

The final score decision interval may be automatically decided, or the final score at the point in time as instructed may be decided by an instruction. The instruction may be given, for example, at the point in time when the user acquires the still image through the still image acquisition instruction portion 12f (freeze button) as the final score decision time t. Therefore, in this case, the display control unit 76 performs control to display the final score and/or the change over time of the final score in a case where a still image acquisition instruction through the still image acquisition instruction portion 12f is given. The observation target for which the user stores the still image often includes a region of interest. The decision of the final score in such a region and the display thereof on the display 18 contribute to a more appropriate diagnosis of the user, which is preferable.

Next, the display control unit 76 performs control to display the final score and/or the change over time of the final score in real time on the display 18. As a display control method, a method capable of stably displaying a decision result of the final score is preferable. Therefore, examples of the display control method include a method of updating the display of the final score or a method of displaying the change over time of the final score, in a case where the display control unit 76 displays a final score having the largest numerical value among the final scores from the observation start and a final score larger than the previous numerical values is obtained.

It is preferable to display the change over time of the final score as a graph in a case of displaying the change over time of the final score. It is preferable that the change over time of the final score is displayed by at least one graph showing a relationship between the final score and the final score decision time, as the graph. In a case of displaying the change over time of the final score by a graph, it is preferable to set a threshold value in advance for the final score value and display the final score on the graph only in a case where the final score value is the threshold value or more.

Figure 13:
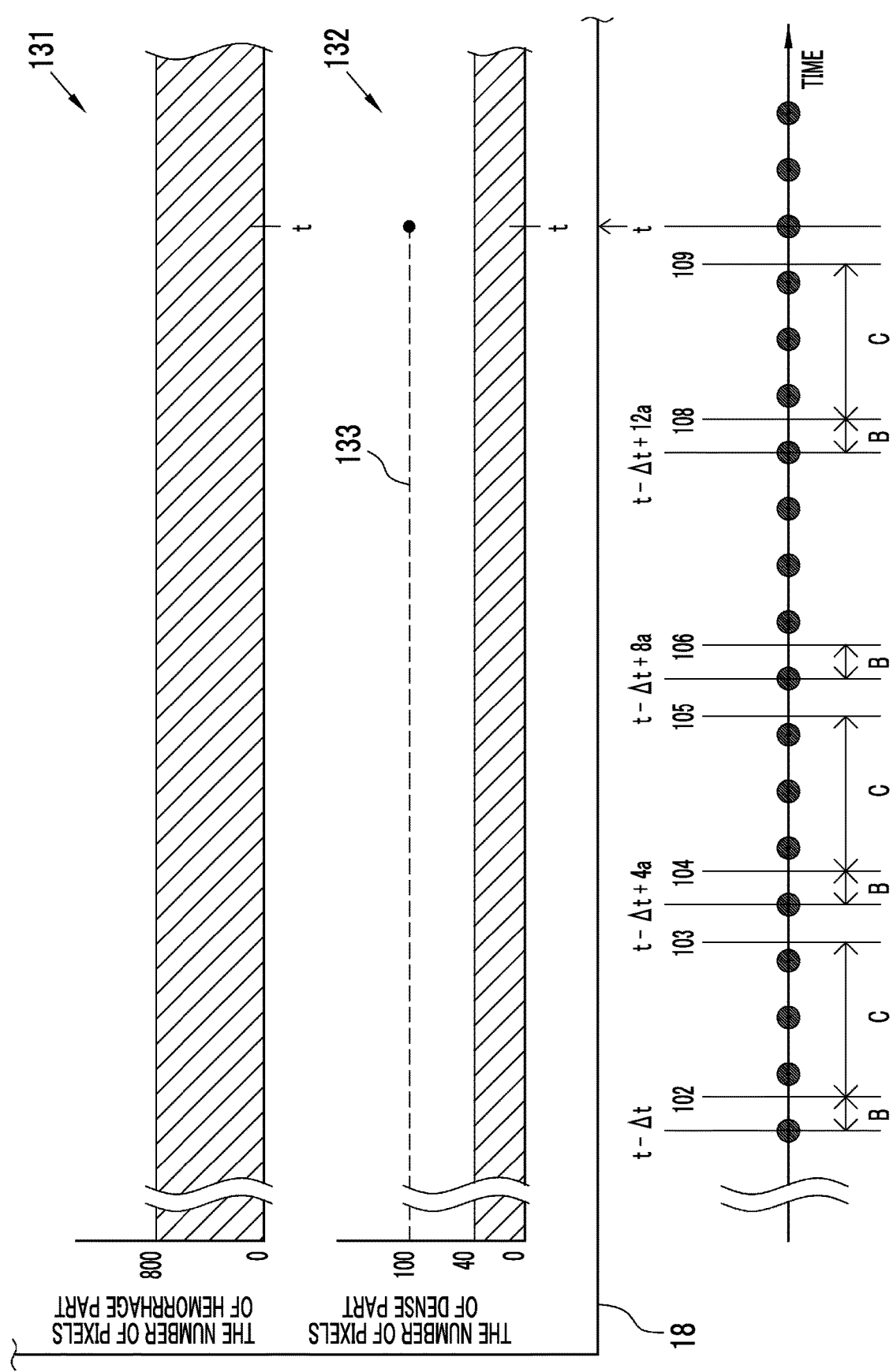
FIG. 13 is a diagram illustrating display control of a final score obtained by a moving average of raw scores.

As shown in FIG. 13, the display control unit 76 performs control as to whether or not to display the final score with the threshold value at the final score decision time t described above. In a case where there are two types of final scores, two types of graphs are displayed on the display 18. In the final score, a threshold value T1 for the number of pixels of the hemorrhage part is set to 800, and a threshold value T2 for the number of pixels of the dense part is set to 40. Since the final score of the number of pixels of the hemorrhage part at the final score decision time t is 120, the final score is smaller than 800 of the threshold value T1. Therefore, the number of pixels of the hemorrhage part at the final score decision time t is not plotted on a graph 131 of the number of pixels of the hemorrhage part, which is the final score. Further, since the final score of the number of pixels of the dense part at the final score decision time t is 100, the final score is larger than 40 of the threshold value T2. Therefore, the number of pixels of the dense part at the final score decision time t is plotted with an auxiliary line 133 on a graph 132 of the number of pixels of the dense part, which is the final score, so that the numerical value can be grasped at a glance. In the graph 131 and the graph 132 of FIG. 13, the threshold value T1 or the threshold value T2 is indicated by diagonal lines.

The display control unit 76 performs control to display the final score and/or the change over time of the final score in real time on the display 18, so that the user can grasp at a glance which item the disease is considered to be most exacerbated in while observing the observation target. Further, the change over time is shown in a graph, so that it is possible to grasp the approximate position of a part where the disease is most exacerbated. Further, since only the item in which the disease is considered to be most exacerbated is displayed through the control of the display of the final score with the threshold value, the display of the final score can be made more stable.

Further, as the control of the display of the final score using the threshold value, for example, the graph displayed on the display 18 may be limited to one in a case where there are two or more types of final scores. Specifically, for example, in a case where one out of the two types of final scores is the threshold value or more and the other is less than the threshold value, only the graph of the final score of the threshold value or more is displayed. The types of parameters such as the final score are carefully selected and displayed, so that the reliability or the stability of the displayed final score is improved. In addition, the user can grasp information for diagnosing the severity or the stage at a glance.

Figure 14:
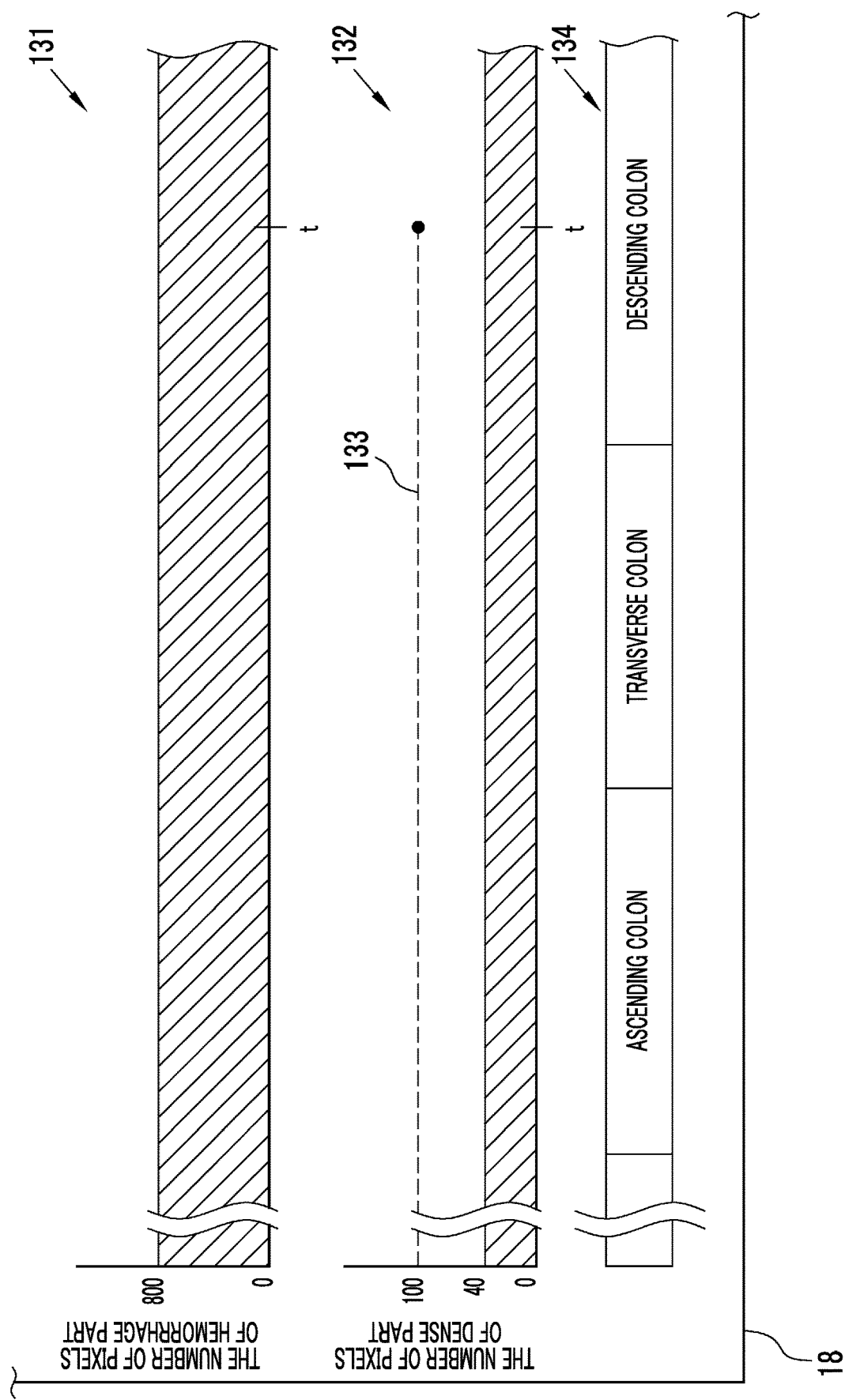
FIG. 14 is a diagram illustrating display control of a final score in which a site name is displayed.

The site determination unit 77 (see FIG. 8) that determines the site of the observation target included in the endoscopic image by performing image analysis on the endoscopic image may be provided, and the change over time of the final score may be displayed by the graph showing a relationship between the final score, and the final score decision time and the site. With this, the image analysis on the endoscopic image is automatically performed, and the site name is displayed in association with the display of the change over time of the final score. As shown in FIG. 14, for example, in a case of performing screening while pulling the endoscope from the part of the cecum, which is positioned at the deep part of the large intestine, in the observation of the large intestine, a site name 134, such as "cecum, ascending colon, transverse colon, descending colon, sigmoid colon, and rectum", is displayed. In this way, the site name 134 is displayed so that it is possible to grasp the part where the disease is exacerbated in the observation without omission, which is preferable.

Figure 15:
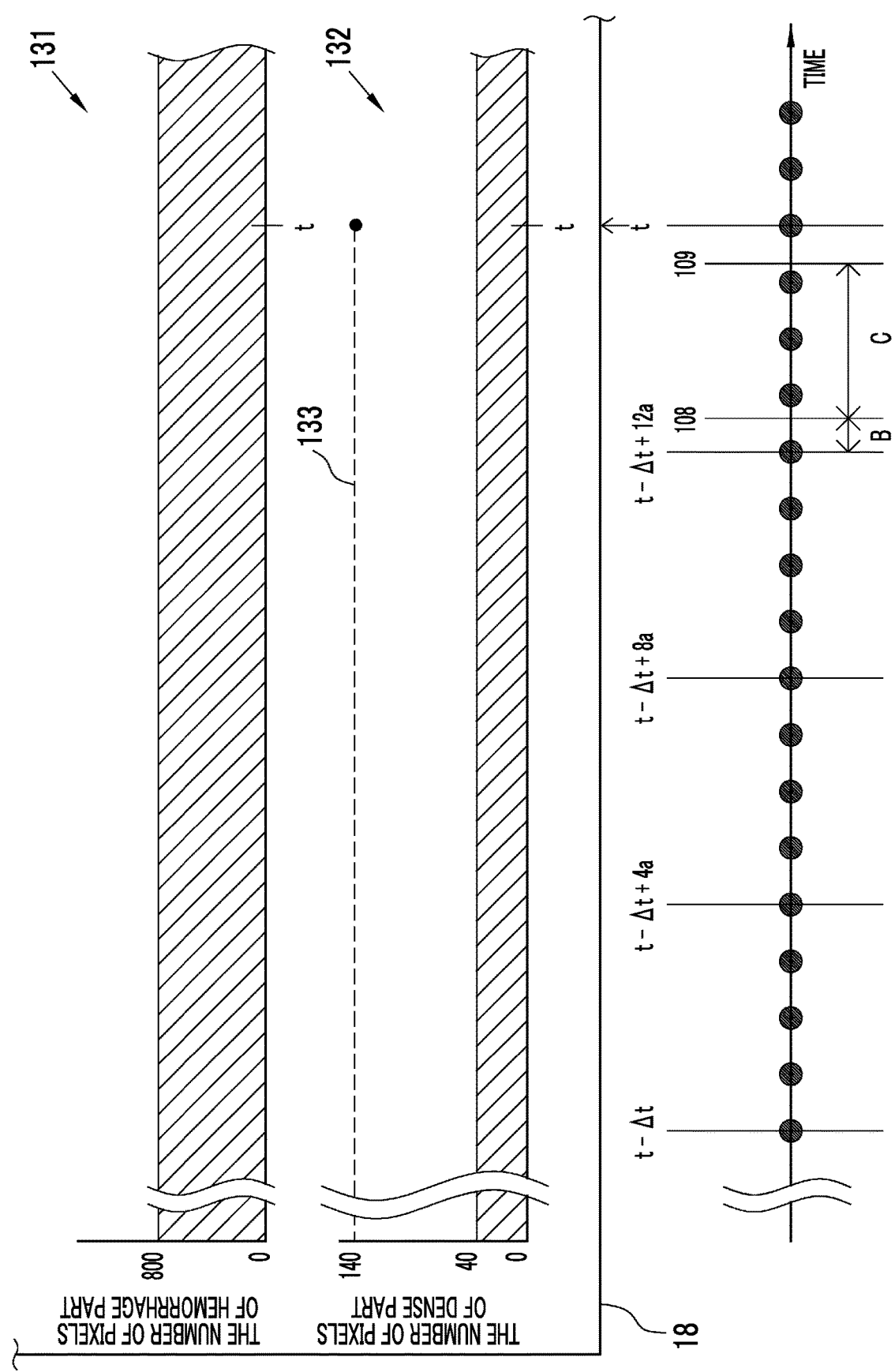
FIG. 15 is a diagram illustrating display control of a final score based on the raw score obtained immediately before.

The final score decision unit 73 may decide the final score on the basis of the raw score calculated immediately before or immediately after the point in time at which the final score is decided. The decision of the final score in these cases will be described in detail with reference to FIGS. 15 and 16. As shown in FIG. 15, in the method of deciding the final score in which the final score is decided on the basis of the raw score calculated immediately before the point in time at which the final score is decided, the final score is decided on the basis of the raw score calculated immediately before the point in time at which the final score is decided, instead of using the plurality of raw scores for the decision. That is, the raw score calculated immediately before the point in time at which the final score is decided is decided as the final score.

The endoscopic image acquisition and the raw score acquisition are the same as described above.

Since the raw scores calculated immediately before the final score decision time t are "the number of pixels of the hemorrhage part: 140" and "the number of pixels of the dense part: 140", which are calculated at the time of the raw score calculation 109 on the basis of the endoscopic image acquired by the endoscopic image acquisition at time t−Δt+ 12a, the final scores are "the number of pixels of the hemorrhage part: 140, the number of pixels of the dense part: 140". The display of the final score using the threshold value through the display control unit 76 is the same as described above. Therefore, as shown in FIG. 15, the display 18 displays the graph 132 of the number of pixels of the dense part in which the number of pixels of the dense part is plotted at 140 as the final score.

Figure 16:
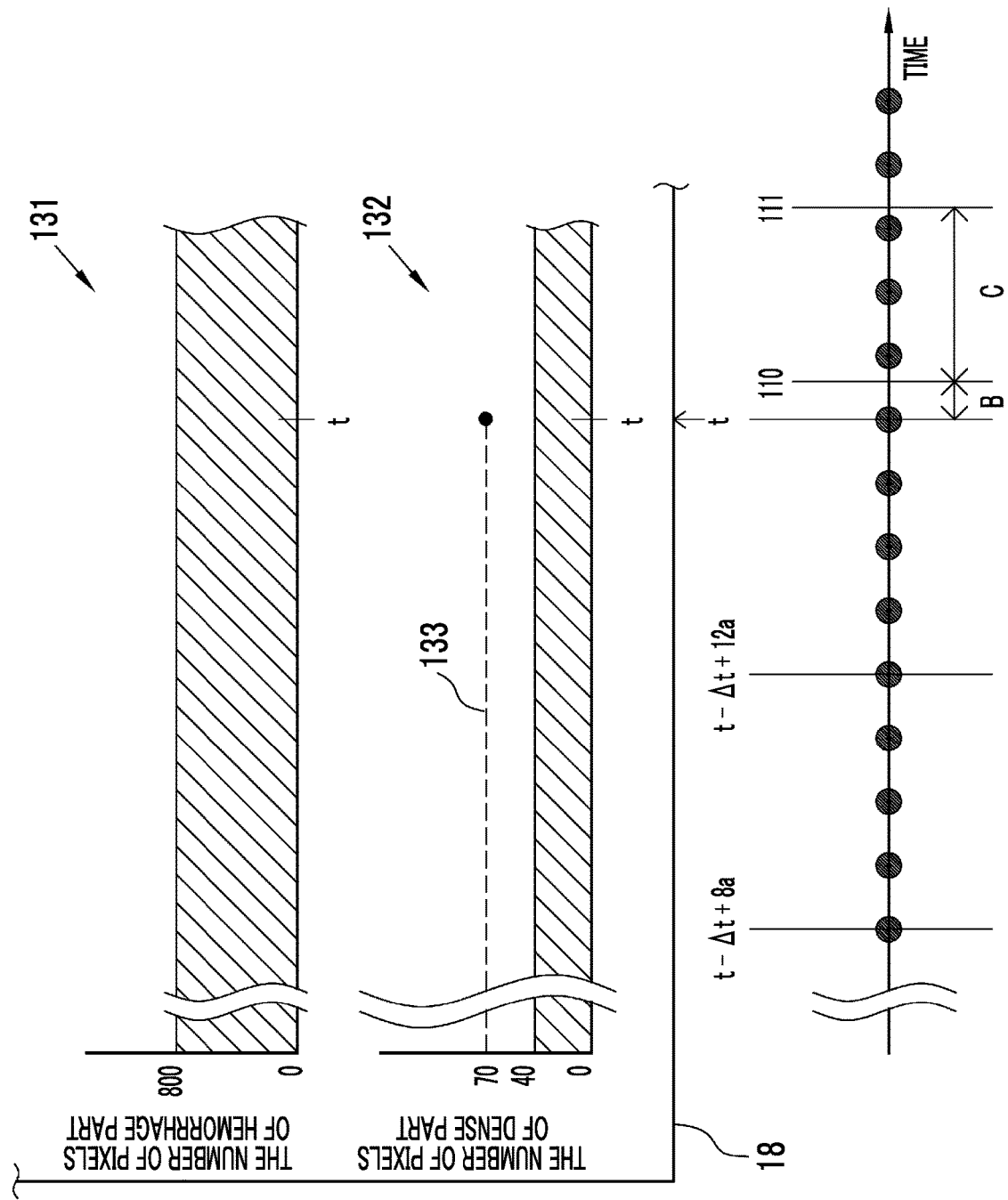
FIG. 16 is a diagram illustrating display control of a final score based on the raw score obtained immediately after.

Alternatively, as shown in FIG. 16, in the method of deciding the final score in which the final score is decided on the basis of the raw score calculated immediately after the point in time at which the final score is decided, the final score is decided on the basis of the raw score calculated immediately after the final score decision time t, instead of using the plurality of raw scores for the decision. That is, the raw score calculated immediately after the final score decision time t is decided as the final score. This is the raw score calculated for the endoscopic image acquired at the final score decision time t. The endoscopic image acquisition and the raw score acquisition are the same as described above.

Since the raw scores calculated immediately after the final score decision time t are "the number of pixels of the hemorrhage part: 160" and "the number of pixels of the dense part: 70", which are calculated at the time of the raw score calculation 111 on the basis of the endoscopic image acquired by the endoscopic image acquisition at time t, the final scores are "the number of pixels of the hemorrhage part: 160, the number of pixels of the dense part: 70". The display of the final score using the threshold value through the display control unit 76 is the same as described above. Therefore, as shown in FIG. 16, the display 18 displays the graph 132 of the number of pixels of the dense part in which the number of pixels of the dense part is plotted at 70 as the final score.

The method of deciding the final score on the basis of the raw score calculated immediately before or immediately after the point in time at which the final score is decided is suitable in a case where it is desired to grasp the final score of the observation target currently being observed. Moreover, the latest final score can be stably displayed, which is suitable.

Further, in a case where the final score is decided at the point in time when the user acquires the still image through the still image acquisition instruction portion 12f, a method of deciding the final score on the basis of the raw score calculated immediately before or immediately after the point in time at which the final score is decided is combined with the above case so that it is possible to quickly and stably display the final score based on the observation site which is a region of interest of the user and for which the still image acquisition instruction is given. Therefore, the display of the final score at the timing when the user wants to obtain information regarding the diagnosis answers the user's needs, which is preferable.

The final score decision unit 73 may decide whether to calculate the final score or define the final score to be uncalculated from the number of the raw scores discriminated to be uncalculated by the unsuitable image discrimination unit 74 and the number of calculated raw scores, among the raw scores based on the plurality of endoscopic images acquired in a predetermined period. Specifically, the final score is defined to be "uncalculated" in a case where, among the raw scores based on the plurality of endoscopic images acquired in the predetermined period, the number of the raw scores except for the raw score to be uncalculated is a predetermined number or less, a case where the number of the raw scores to be uncalculated is a predetermined number or more, a case where a ratio of the number of the raw scores to be uncalculated to the number of the raw scores based on the plurality of endoscopic images acquired in the predetermined period is a predetermined value or more, or the like.

Figure 17:
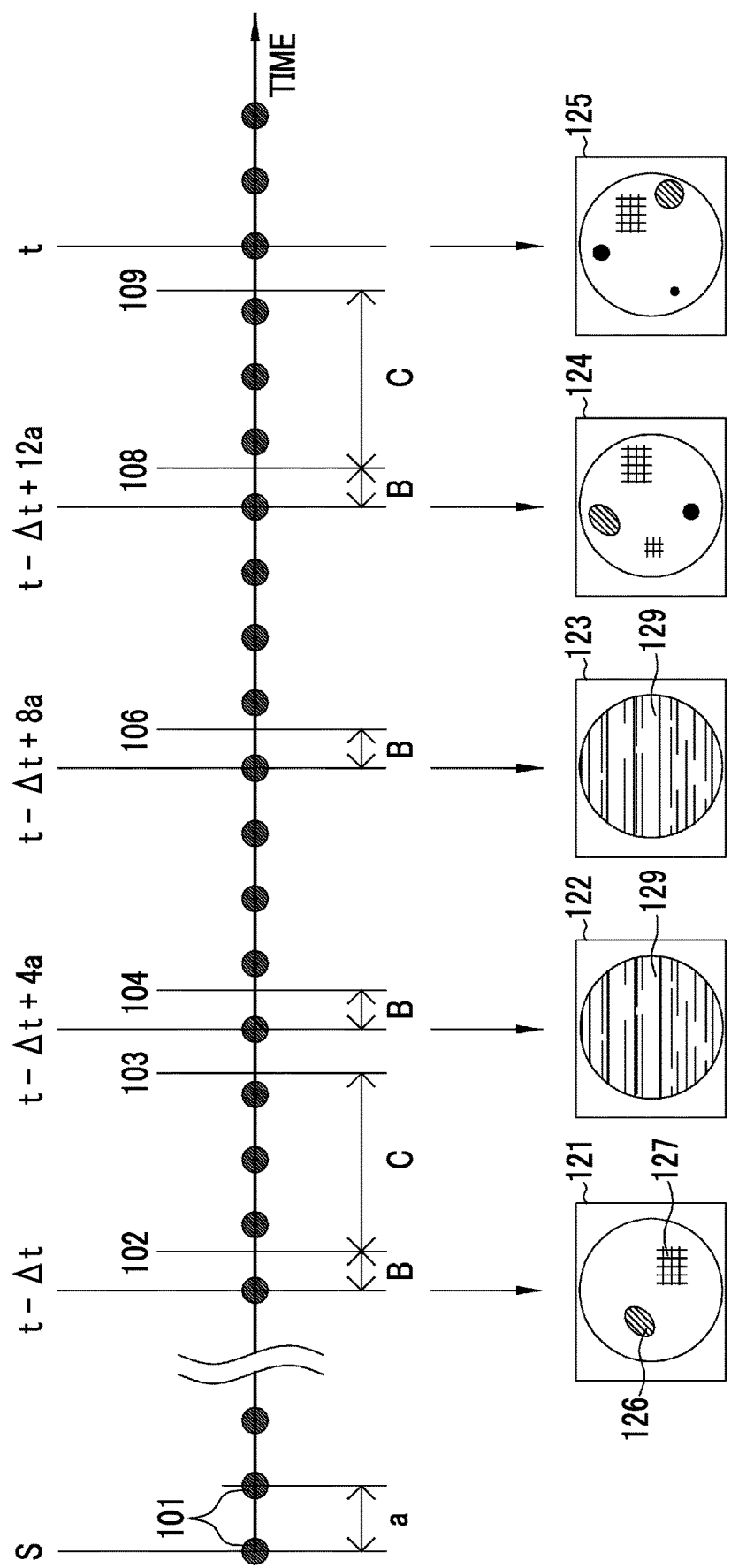
FIG. 17 is a diagram illustrating relation between the endoscopic image and calculation of a raw score to be uncalculated in time series.
Figure 18:
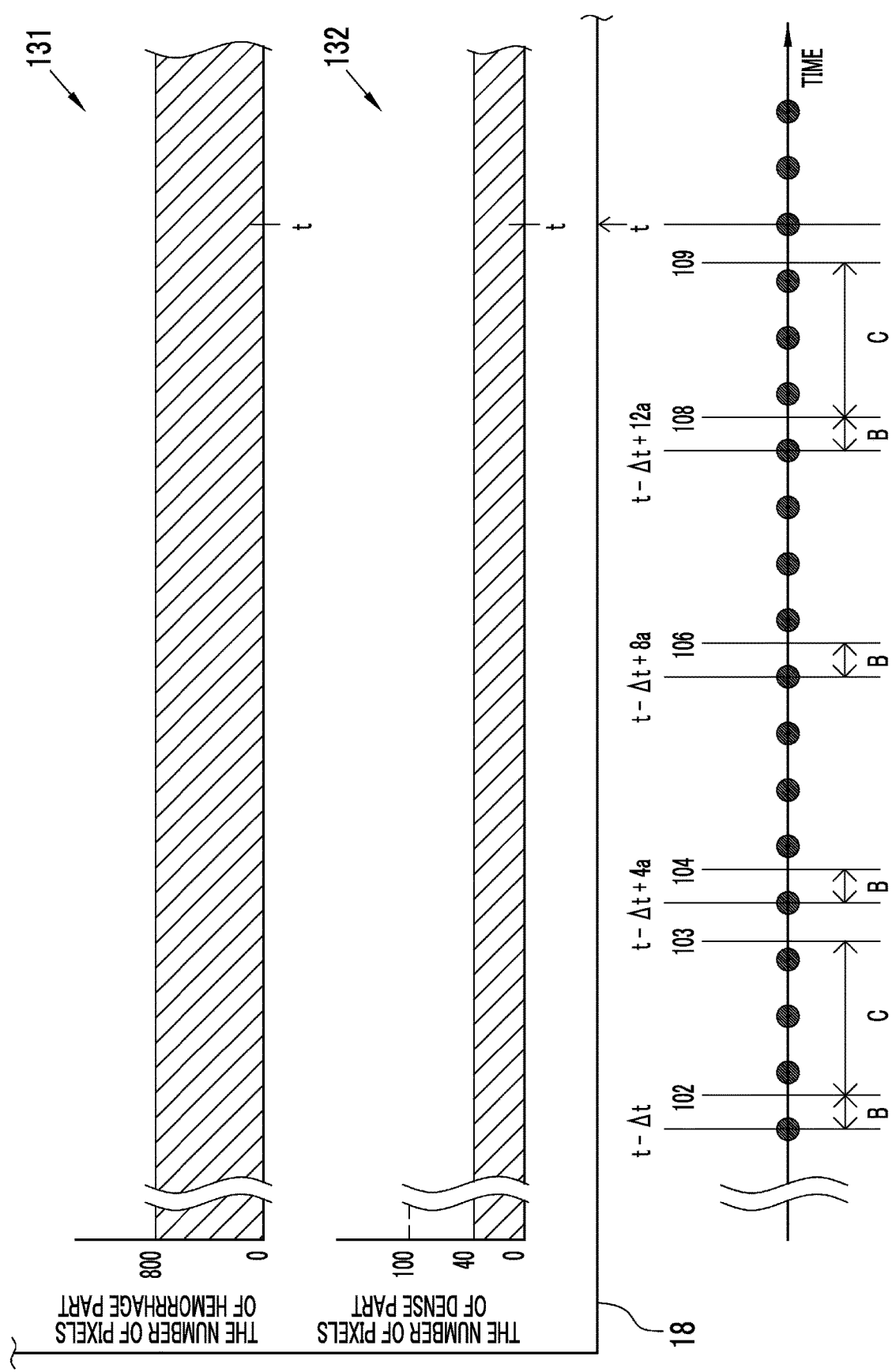
FIG. 18 is a diagram illustrating display control of a final score in a case where the raw score to be uncalculated is included.

The decision of the final score in this case will be described in detail with reference to FIGS. 17 and 18. As shown in FIG. 17, the endoscopic image acquisition 101 is automatically performed at the image acquisition interval a in the period Δt, which is a predetermined period, and the endoscopic images are acquired at time t−Δt, time t−Δt+4a, time t−Δt+8a, and time t−Δt+12a. As soon as the endoscopic image is acquired, the unsuitable image discrimination unit 74 discriminates whether the endoscopic image acquired at each time after the period B is suitable or unsuitable for the calculation of the raw score. The endoscopic images 122 and 123 acquired at time t−Δt+4a and time t−Δt+8a, among the plurality of endoscopic images, are the unclear images 129. Therefore, the raw score calculation unit 72 defines the raw score to be "uncalculated" for each of the endoscopic images 122 and 123.

In the present embodiment, in a case where the number of the raw scores except for the raw score to be uncalculated is two or less, among the raw scores based on the plurality of endoscopic images acquired in the predetermined period, the final score is defined to be "uncalculated". Therefore, the case where the number of the plurality of endoscopic images is four, the number of the raw scores to be uncalculated is two, and the number of the raw scores except for the raw scores to be uncalculated is two corresponds to "a case where the number of the raw scores except for the raw scores to be uncalculated is two or less". Therefore, the final score at the final score decision time t is defined to be "uncalculated". The display control unit 76 performs control not to display the final score to be uncalculated, on the display. Therefore, as shown in FIG. 18, the display 18 does not plot the final score on both the graph 131 and the graph 132.

In the above case shown in FIG. 17, in a case where a method of defining the final score to be "uncalculated" when the number of the raw scores to be uncalculated is a predetermined number or more is adopted, the final score is defined to be "uncalculated" because the number of the raw scores to be uncalculated is two, for example, in a case where the predetermined number is set to two. Similarly, in a case where a method of defining the final score to be "uncalculated" when the ratio of the number of the raw scores to be uncalculated to the number of the raw scores based on the plurality of endoscopic images acquired in the predetermined period is a predetermined value or more is adopted, for example, when the predetermined value is set to 0.5, the final score is defined to be "uncalculated" because the number of the endoscopic images acquired in the period Δt, that is, the number of the raw scores acquired in the period Δt is four, the number of the raw scores to be "uncalculated", among them, is two, and the above ratio is 2/4 (0.5).

As described above, whether to calculate the final score or define the final score to be uncalculated is decided from the number of the raw scores discriminated to be uncalculated by the unsuitable image discrimination unit 74 and the number of the calculated raw scores so that the number or the ratio of raw scores, which are not preferable, is restrained from being used, the final score is appropriately decided, and the score is stably displayed, which is preferable.

The final score may be displayed by a message for giving notice of the determination result of the severity or the stage of the disease of the observation target. The severity or the stage is determined by the final score. For example, the display control unit 76 uses a threshold value for performing control as to whether or not to display the final score. That is, in the final score, the severity or the stage is determined by the threshold value T1 of the number of pixels of the hemorrhage part and the threshold value T2 of the number of pixels of the dense part. With regard to the severity, a case where the number of pixels of the hemorrhage part is the threshold value T1 or more is determined to be severe, a case where the number of pixels of the hemorrhage part is less than the threshold value T1 and the number of pixels of the dense part is the threshold value T2 or more is determined to be moderate, or a case where the number of pixels of the hemorrhage part is less than the threshold value T1 and the number of pixels of the dense part is less than the threshold value T2 is determined to be mild. With regard to the stage, a case where a determination is made to be severe when the number of pixels of the hemorrhage part is the threshold value T1 or more and a case where a determination is made to be moderate when the number of pixels of the hemorrhage part is less than the threshold value T1 and the number of pixels of the dense part is the threshold value T2 or more are determined as pathological non-remission, or a case where a determination is made to be mild when the number of pixels of the hemorrhage part is less than the threshold value T1 and the number of pixels of the dense part is less than the threshold value T2 is determined as the pathological remission.

Figure 19:
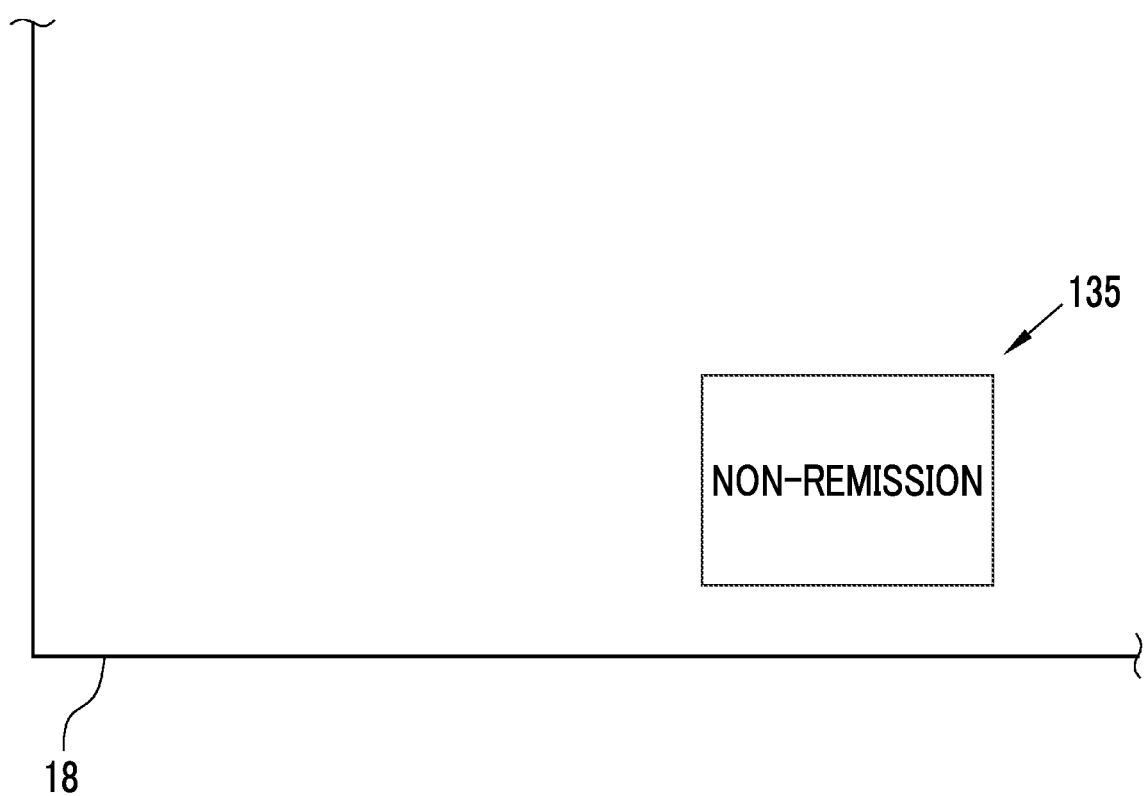
FIG. 19 is a diagram illustrating display control of a final score showing a discrimination result.

As shown in FIG. 19, a message for giving notice of the determination result of the severity or the stage is displayed, for example, by displaying a message 135 on a part of the display 18. In addition to "non-remission", the message 135 is any one of message "severe", "moderate", or "mild" in the case of the severity, and any one of message "remission" or "non-remission" in the case of the stage. The final score is displayed as a message for giving notice of the determination result of the severity or the stage of the disease so that the user can obtain information for supporting the diagnosis of the severity or the stage at a glance without interruption of the observation, which is preferable.

Figure 20:
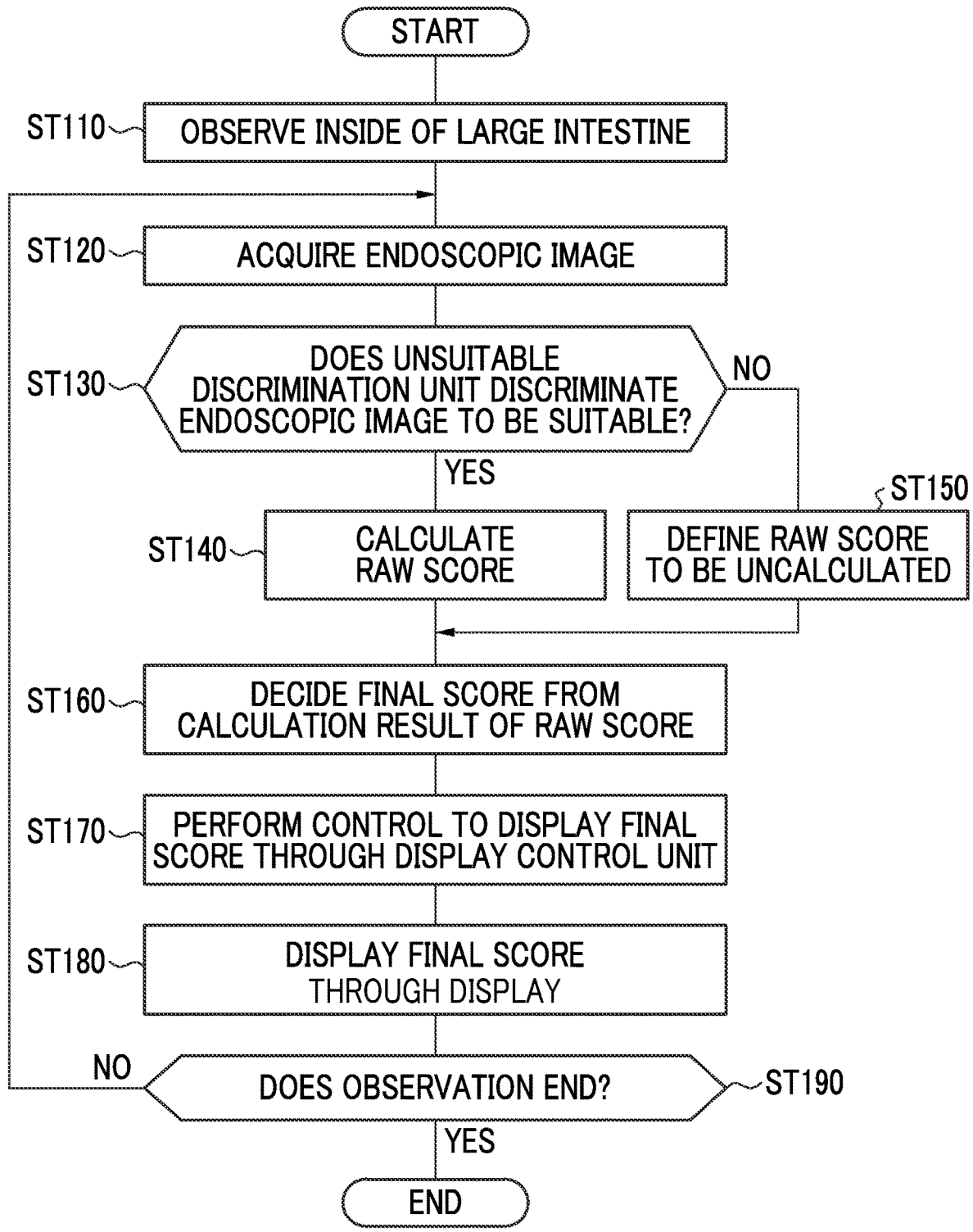
FIG. 20 is a flowchart showing a series of flows of a score display mode.

Next, a series of flows of the score display mode will be described with reference to the flowchart shown in FIG. 20. In a case where a mode is switched to the score display mode, the observation target is irradiated with special light. The endoscope 12 picks up the image of the observation target illuminated with special light (step ST110), thereby obtaining an endoscopic image, which is a special image captured at a certain point in time. In this flowchart, the final scores are set to be automatically acquired at a predetermined interval. The image acquisition unit 71 acquires the special image from the endoscope 12 (step ST120).

The special image is sent to the unsuitable image discrimination unit 74, and whether the special image is suitable or unsuitable for the calculation of the raw score is discriminated. In a case of a special image discriminated to be suitable (YES in step ST130), the raw score is calculated on the basis of the special image (step ST140). In a case of a special image discriminated to be unsuitable (NO in step ST130), the raw score is defined to be "uncalculated" (step ST150).

The final score is decided from the calculation result of the raw score (step ST160). In a case where the final score is decided, the display control unit 76 controls the display of the final score (step ST170). The display displays the final score in a controlled display (step ST180). In a case of ending the observation (YES in step ST190), the observation ends. In a case of not ending the observation (NO in step ST190), the process returns to the endoscopic image acquisition.

In the above embodiment, the present invention is applied to the endoscope system that performs processing on the endoscopic image, but the present invention can also be applied to a medical image processing system that processes medical images other than the endoscopic image. In this case, the medical image processing system includes the image processing device of the embodiment of the present invention. Further, the present invention can also be applied to a diagnosis support device that is used to provide diagnosis support to the user by using medical images. The present invention can also be applied to a medical service support device that is used to support the medical service, such as a diagnostic report, by using medical images.

Figure 21:
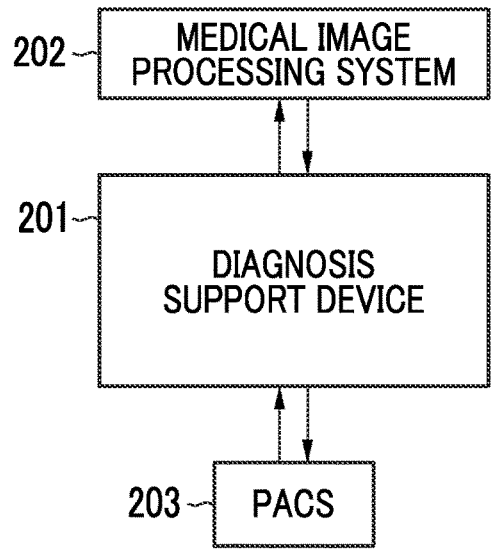
FIG. 21 is a block diagram showing a diagnosis support device.
Figure 22:
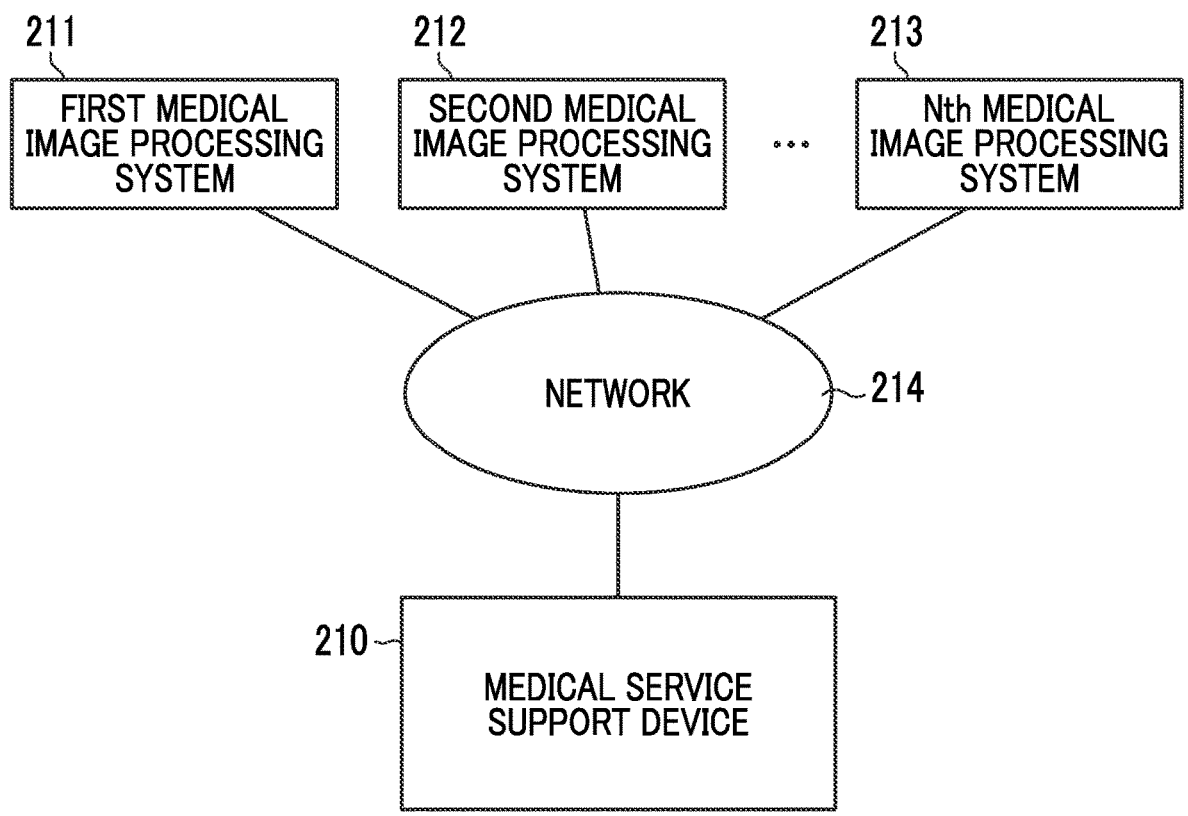
FIG. 22 is a block diagram showing a medical service support device.

For example, as shown in FIG. 21, a diagnosis support device 201 is used in combination with the modality, such as a medical image processing system 202, and picture archiving and communication systems (PACS) 203. As shown in FIG. 22, a medical service support device 210 is connected to various examination apparatuses such as a first medical image processing system 211, a second medical image processing system 212, . . . , and an Nth medical image processing system 213 through any network 214. The medical service support device 210 receives medical images from the first medical image processing system 211, the second medical image processing system 212, . . . , the Nth medical image processing system 213, and supports the medical service on the basis of the received medical images.

In the above embodiment, the hardware structures of the processing units that execute various types of processing, such as the image signal acquisition unit 51, the DSP 52, the noise reduction unit 53, the signal processing unit 55, and the video signal generation unit 56, which are included in the processor device 16, are various processors to be described below. The various processors include, for example, a central processing unit (CPU), which is a general-purpose processor that executes software (programs) to function as various processing units, a programmable logic device (PLD), such as a field programmable gate array (FPGA), which is a processor having a changeable circuit configuration after manufacture, and a dedicated electrical circuit, which is a processor having a dedicated circuit configuration designed to execute various types of processing.

One processing unit may be formed of one of these various processors, or may be formed of a combination of two or more processors of the same type or different types (for example, a plurality of FPGAs, or a combination of a CPU and an FPGA). Alternatively, a plurality of processing units may be formed of one processor. A first example in which a plurality of processing units are formed of one processor is an aspect in which one or more CPUs and software are combined to constitute one processor and the processor functions as a plurality of processing units, as typified by a computer such as a client or a server. A second example is an aspect in which a processor that realizes all of the functions of a system including the plurality of processing units with one integrated circuit (IC) chip is used, as typified by a system on chip (SoC) or the like. In this manner, various processing units are formed of one or more of the above-described various processors as hardware structures.

More specifically, the hardware structures of these various processors are electrical circuitry in which circuit elements such as semiconductor elements are combined.

The present invention can also be implemented by the following another embodiment.

A processor device is provided. The processor device
   acquires a plurality of endoscopic images obtained by picking up images of an observation target at times different from each other with an endoscope device,
   calculates a raw score related to a determination of a severity or a stage of a disease of the observation target, on the basis of each of the endoscopic images,
   decides a final score on the basis of the raw score, and
   performs control to display the final score and/or a change over time of the final score in real time on a display.

EXPLANATION OF REFERENCES

10: endoscope system
12: endoscope
12*a*: insertion part
12*b*: operation part
12*c*: bendable portion
12*d*: distal end portion
12*e*: angle knob
12*f*: still image acquisition instruction portion
12*g*: mode changeover switch
12*h*: zoom operation portion
14: light source device
16: processor device (image processing device)
18: display
19: console
20: light source unit
20*a*: V-LED
20*b*: B-LED
20*c*: G-LED
20*d*: R-LED
21: light source control unit
30*a*: illumination optical system
30*b*: image pickup optical system
41: light guide
42: illumination lens
43: objective lens
44: zoom lens
45: image pickup sensor
46: CDS/AGC circuit
47: A/D converter
51: image signal acquisition unit
52: DSP
53: noise reduction unit
54: memory
55: signal processing unit
56: video signal generation unit
61: normal image generation unit
62: special image generation unit
63: score processing unit
71: image acquisition unit
72: raw score calculation unit
73: final score decision unit
74: unsuitable image discrimination unit
75: image storage unit
76: display control unit
77: site determination unit 81: first calculation unit
82: second calculation unit
83: first discrimination unit
84: second discrimination unit
85: superficial blood vessels
86: intramucosal hemorrhage
87: extramucosal hemorrhage
101: endoscopic image acquisition
102, 104, 106, 108, 110, 111: unsuitable image discrimination
103, 105, 107, 109: raw score calculation
121 to 125: endoscopic image
126: intramucosal hemorrhage part
127: blood vessel dense part
128: extramucosal hemorrhage part
129: unclear image
131, 132: graph
133: auxiliary line
134: site name
135: message
201: diagnosis support device
202: medical image processing system
203: PACS
210: medical service support device
211: first medical image processing system
212: second medical image processing system
213: Nth medical image processing system
214: network
t: final score decision time
ST110 to ST190: step

What is claimed is:

1. An image processing device comprising:
a processor configured to:
   acquire a plurality of endoscopic images obtained by picking up images of an observation target at times different from each other with an endoscope;
   discriminate, for each endoscopic image, whether the endoscopic image is suitable or unsuitable for calculation of a raw score;
   calculate the raw score related to a severity or a stage of a disease of the observation target, on the basis of the plurality of the endoscopic images;
   define the raw score to be uncalculated for the endoscopic image discriminated to be unsuitable for the calculation of the raw score;
   decide a final score on the basis of the raw score that is calculated on the basis of a plurality of the endoscopic images acquired in a predetermined period before a point in time at which the final score is decided, and define the final score to be uncalculated in a case where the number of the raw scores except for the raw score to be uncalculated is a predetermined number or less, a case where the number of the raw scores to be uncalculated is a predetermined number or more, or a case where a ratio of the number of the raw scores to be uncalculated to the number of the raw scores based on the plurality of endoscopic images acquired in the predetermined period is a predetermined value or more, the raw scores being based on the plurality of endoscopic images acquired in the predetermined period; and
   perform control to display a change over time of the final score in real time on a display.

2. The image processing device according to claim 1, wherein the processor is configured to calculate two or more types of raw scores different from each other.

3. The image processing device according to claim 1, wherein the processor is configured to calculate the raw score on the basis of a first feature amount obtained by analyzing the endoscopic image.

4. The image processing device according to claim 3, wherein the first feature amount is an amount related to a superficial blood vessel dense part, an intramucosal hemorrhage part, or an extramucosal hemorrhage part included in the endoscopic image.

5. The image processing device according to claim 1, wherein the processor is configured to calculate the raw score with a trained first machine learning model generated by an input of a past endoscopic image associated with the raw score to a machine learning model.

6. The image processing device according to claim 1, wherein the processor is configured to decide the final score from the raw score that is calculated on the basis of a plurality of the endoscopic images acquired in a predetermined period before a point in time at which the final score is decided.

7. The image processing device according to claim 6, wherein the processor is configured to decide the final score by performing a moving average, or FIR filtering or IIR filtering of a plurality of the raw scores.

8. The image processing device according to claim 1, wherein the processor is configured to decide the final score on the basis of the raw score calculated immediately before or immediately after a point in time at which the final score is decided.

9. The image processing device according to claim 1, wherein the processor is configured to discriminate whether the endoscopic image is suitable or unsuitable for the calculation of the raw score, on the basis of a second feature amount of the endoscopic image.

10. The image processing device according to claim 9, wherein the second feature amount is an amount related to at least one of halation distribution, spatial frequency distribution, brightness value distribution, shadow distribution, a magnification ratio indicator, and reflected light distribution of illumination light of the endoscopic image, the illumination light being emitted to the observation target.

11. The image processing device according to claim 9, wherein the processor is configured to discriminate whether the endoscopic image is suitable or unsuitable for the calculation of the raw score with a trained second machine learning model generated by an input of a past endoscopic image to a machine learning model, the past endoscopic image being associated with whether the endoscopic image is suitable or unsuitable for the calculation of the raw score.

12. The image processing device according to claim 1, wherein the processor is configured to decide the final score on the basis of the raw score except for the raw score to be uncalculated.

13. The image processing device according to claim 1, wherein the change over time of the final score is displayed by at least one graph showing a relationship between the final score and a decision time of the final score.

14. The image processing device according to claim 1, wherein the processor is configured to determine a site of the observation target included in the endoscopic image by performing image analysis on the endoscopic image, and the change over time of the final score is displayed by at least one graph showing a relationship between the final score, and a decision time of the final score and the site.

15. The image processing device according to claim 1, wherein the processor is configured to:
    give an instruction to acquire a still image; and
    perform control to display the final score and/or the change over time of the final score in a case where the instruction is given.

16. The image processing device according to claim 1, wherein the disease is ulcerative colitis.

17. An endoscope system comprising an image processing device and an endoscope, wherein the image processing device includes a processor configured to:
    acquire a plurality of endoscopic images obtained by picking up images of an observation target at times different from each other with the endoscope;
    discriminate, for each endoscopic image, whether the endoscopic image is suitable or unsuitable for calculation of a raw score;
    calculate the raw score related to a severity or a stage of a disease of the observation target, on the basis of the plurality of the endoscopic images;
    define the raw score to be uncalculated for the endoscopic image discriminated to be unsuitable for the calculation of the raw score;
    decide a final score on the basis of the raw score that is calculated on the basis of a plurality of the endoscopic images acquired in a predetermined period before a point in time at which the final score is decided, and define the final score to be uncalculated in a case where the number of the raw scores except for the raw score to be uncalculated is a predetermined number or less, a case where the number of the raw scores to be uncalculated is a predetermined number or more, or a case where a ratio of the number of the raw scores to be uncalculated to the number of the raw scores based on the plurality of endoscopic images acquired in the predetermined period is a predetermined value or more, the raw scores being based on the plurality of endoscopic images acquired in the predetermined period; and
    perform control to display a change over time of the final score in real time on a display.

18. An image processing method comprising:
    acquiring a plurality of endoscopic images obtained by picking up images of an observation target at times different from each other;
    discriminating, for each endoscopic image, whether the endoscopic image is suitable or unsuitable for calculation of a raw score;
    calculating the raw score related to a determination of a severity or a stage of a disease of the observation target, on the basis of each of the endoscopic images;
    define the raw score to be uncalculated for the endoscopic image discriminated to be unsuitable for the calculation of the raw score;
    deciding a final score on the basis of the raw score that is calculated on the basis of a plurality of the endoscopic images acquired in a predetermined period before a point in time at which the final score is decided, and defining the final score to be uncalculated in a case where the number of the raw scores except for the raw score to be uncalculated is a predetermined number or less, a case where the number of the raw scores to be uncalculated is a predetermined number or more, or a case where a ratio of the number of the raw scores to be uncalculated to the number of the raw scores based on the plurality of endoscopic images acquired in the predetermined period is a predetermined value or more, the raw scores being based on the plurality of endoscopic images acquired in the predetermined period; and
    performing control to display the final score or a change over time of the final score in real time on a display.

* * * * *